US008603105B2

(12) United States Patent
Sauer

(10) Patent No.: US 8,603,105 B2
(45) Date of Patent: Dec. 10, 2013

(54) ERGONOMIC, LIGHTED UTERINE MANIPULATOR WITH CAUTERY

(75) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 67 days.

(21) Appl. No.: 13/165,494

(22) Filed: Jun. 21, 2011

(65) Prior Publication Data

US 2012/0330324 A1  Dec. 27, 2012

(51) Int. Cl.
*A61B 17/42* (2006.01)

(52) U.S. Cl.
USPC .......................................................... 606/119

(58) Field of Classification Search
USPC ............... 606/119, 193, 125, 27–29, 45–48; 600/149, 208, 210, 217, 223, 245, 249, 600/104–107, 153, 184
See application file for complete search history.

(56) References Cited

U.S. PATENT DOCUMENTS

| | | | | |
|---|---|---|---|---|
| 3,877,433 | A * | 4/1975 | Librach | 606/119 |
| 3,945,371 | A | 3/1976 | Adelman | |
| 3,948,270 | A | 4/1976 | Hasson | |
| 4,000,743 | A * | 1/1977 | Weaver | 606/119 |
| 4,022,208 | A * | 5/1977 | Valtchev | 604/515 |
| 4,337,763 | A | 7/1982 | Petrassevich | |
| 4,449,519 | A | 5/1984 | Sarrine | |
| 4,562,832 | A | 1/1986 | Wilder et al. | |
| 4,597,383 | A | 7/1986 | VanDerBel | |
| 4,901,708 | A | 2/1990 | Lee | |
| 5,131,380 | A | 7/1992 | Heller et al. | |
| 5,143,054 | A | 9/1992 | Adair | |
| 5,209,754 | A * | 5/1993 | Ahluwalia | 600/207 |
| 5,382,252 | A * | 1/1995 | Failla et al. | 606/119 |
| 5,394,863 | A | 3/1995 | Sanford et al. | |
| 5,443,058 | A * | 8/1995 | Ough | 600/188 |
| 5,445,643 | A * | 8/1995 | Valtchev | 606/119 |
| 5,464,409 | A * | 11/1995 | Mohajer | 606/119 |
| 5,487,377 | A * | 1/1996 | Smith et al. | 600/204 |
| 5,520,698 | A * | 5/1996 | Koh | 606/119 |
| 5,556,401 | A * | 9/1996 | Caillouette | 606/119 |
| 5,643,285 | A * | 7/1997 | Rowden et al. | 606/119 |
| 5,840,077 | A | 11/1998 | Rowden et al. | |
| 5,951,465 | A * | 9/1999 | Schiff et al. | 600/224 |
| 6,059,719 | A * | 5/2000 | Yamamoto et al. | 600/127 |
| 6,572,631 | B1 * | 6/2003 | McCartney | 606/167 |
| 7,077,803 | B2 * | 7/2006 | Kasahara et al. | 600/104 |

(Continued)

FOREIGN PATENT DOCUMENTS

| | | |
|---|---|---|
| EP | 2 116 202 A1 | 11/2009 |
| WO | 2005/082299 A2 | 9/2005 |
| WO | 2010/151429 A2 | 12/2010 |

OTHER PUBLICATIONS http://www.thefreedictionary.com/mechanism, dictionary definition of the term "mechanism" retrieved May 7, 2013.*

(Continued)

*Primary Examiner* — Ryan Severson
*Assistant Examiner* — David Eastwood

(57) ABSTRACT

A uterine manipulator includes a sound and a body. The sound has a selectively actuatable anchor disposed proximate a distal end and an operating mechanism spaced from the anchor for controlling actuation of the anchor. The body has a passage therethrough adapted to receive the sound passed proximally through the body to a position in which the operating mechanism is accessible proximally of the body and the anchor extends distally.

20 Claims, 19 Drawing Sheets

(56) References Cited

U.S. PATENT DOCUMENTS

| | | | |
|---|---|---|---|
| 2001/0014805 A1* | 8/2001 | Burbank et al. | 606/45 |
| 2001/0021854 A1* | 9/2001 | Donnez et al. | 606/119 |
| 2001/0031964 A1* | 10/2001 | Gentelia et al. | 606/45 |
| 2001/0049509 A1* | 12/2001 | Sekine et al. | 604/264 |
| 2003/0109873 A1* | 6/2003 | Muzzammel | 606/45 |
| 2004/0116955 A1* | 6/2004 | Foltz et al. | 606/193 |
| 2005/0049454 A1* | 3/2005 | Ouchi | 600/105 |
| 2005/0080411 A1* | 4/2005 | Ouchi | 606/45 |
| 2005/0080412 A1* | 4/2005 | Ouchi | 606/45 |
| 2005/0277948 A1* | 12/2005 | Cedars et al. | 606/119 |
| 2005/0288660 A1* | 12/2005 | Ryan et al. | 606/28 |
| 2006/0027241 A1* | 2/2006 | Malecki et al. | 128/898 |
| 2007/0135819 A1* | 6/2007 | Spiritos et al. | 606/119 |
| 2007/0260265 A1* | 11/2007 | Walter | 606/119 |
| 2008/0033237 A1* | 2/2008 | Ouchi | 600/104 |
| 2008/0058605 A1* | 3/2008 | Sorensen | 600/208 |
| 2008/0097468 A1* | 4/2008 | Adams et al. | 606/119 |
| 2009/0131954 A1* | 5/2009 | Christian et al. | 606/119 |
| 2009/0209973 A1* | 8/2009 | East | 606/119 |
| 2009/0318950 A1* | 12/2009 | Gross | 606/193 |
| 2010/0106163 A1* | 4/2010 | Blair et al. | 606/119 |
| 2010/0145224 A1* | 6/2010 | Lee et al. | 600/562 |
| 2010/0305578 A1* | 12/2010 | Auerbach et al. | 606/119 |

OTHER PUBLICATIONS

VCARE® Sterile, Disposable, Easy to Use: directions for use (4 pages).
VCARE® Vaginal-Cervical Ahluwalia Retractor-Elevator: directions for use (2 pages).
The RUMI System™ Uterine Manipulator Injector: directions for use (2 pages).
Uterine Manipulator Description and Specs—Ethicon Endo-Surgery, Inc. (1 page) http://www.ethiconendosurgery.com/clinician/product/endodevices/uterinemanipulator (Jun. 21, 2011).
Marina Medical: Technical Tips (Reusable Manipulators)—2 pages.
CooperSurgical: The KOH Colpotomizer™ System (2 pages).
International Search Report (dated Dec. 18, 2012) in corresponding PCT Patent Application No. PCT/US2012/043596 (4 pages).

* cited by examiner

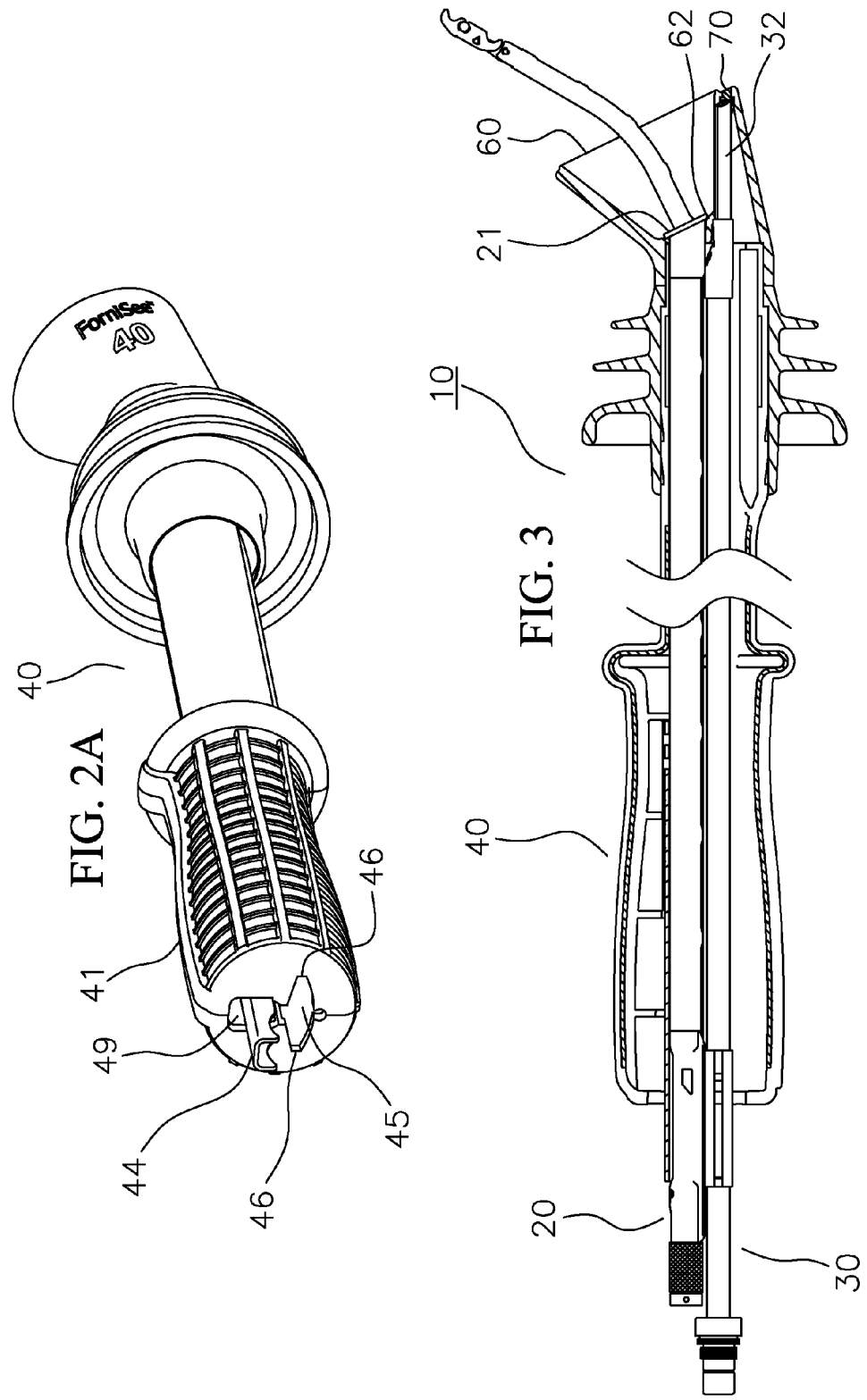

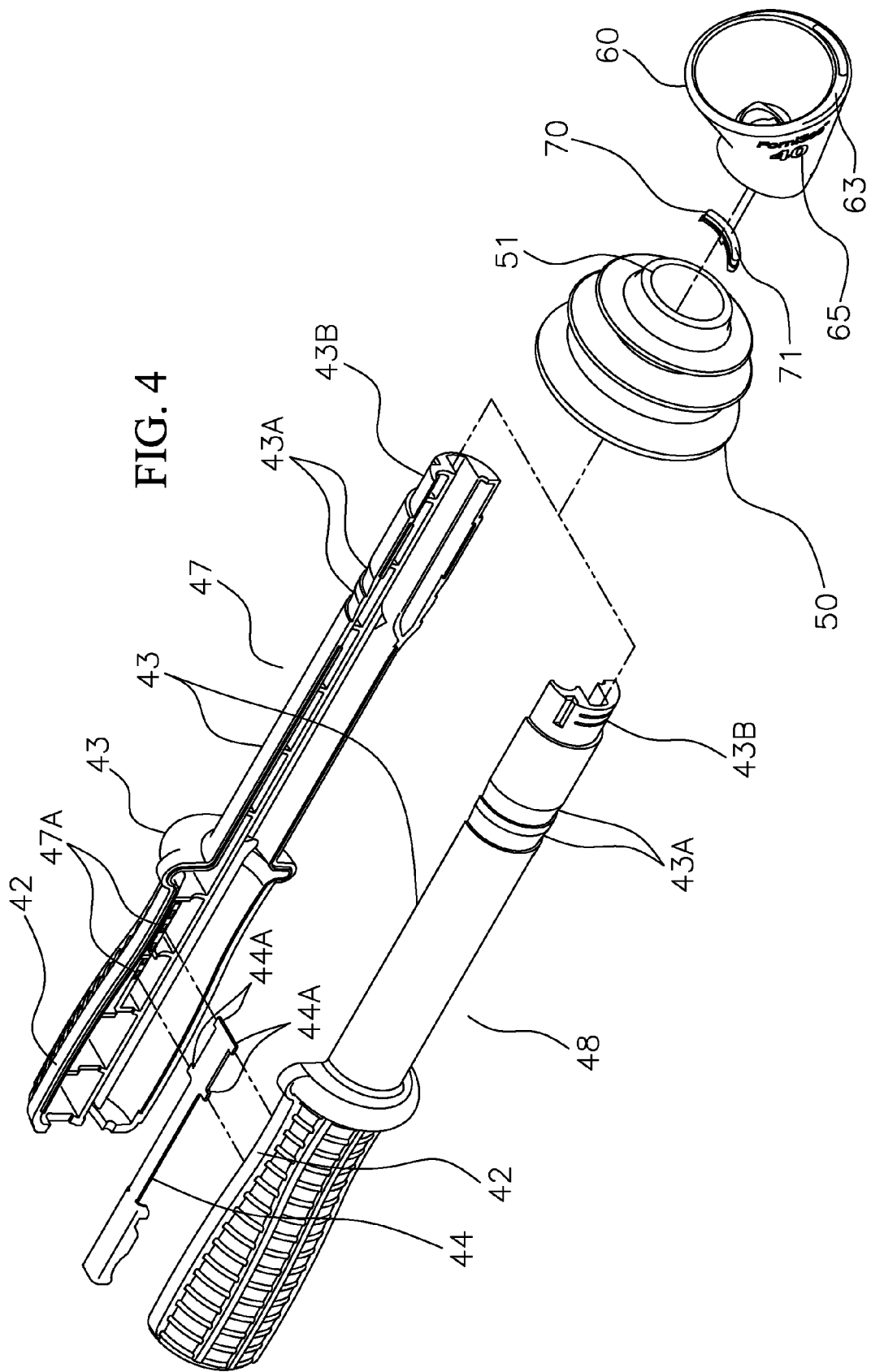

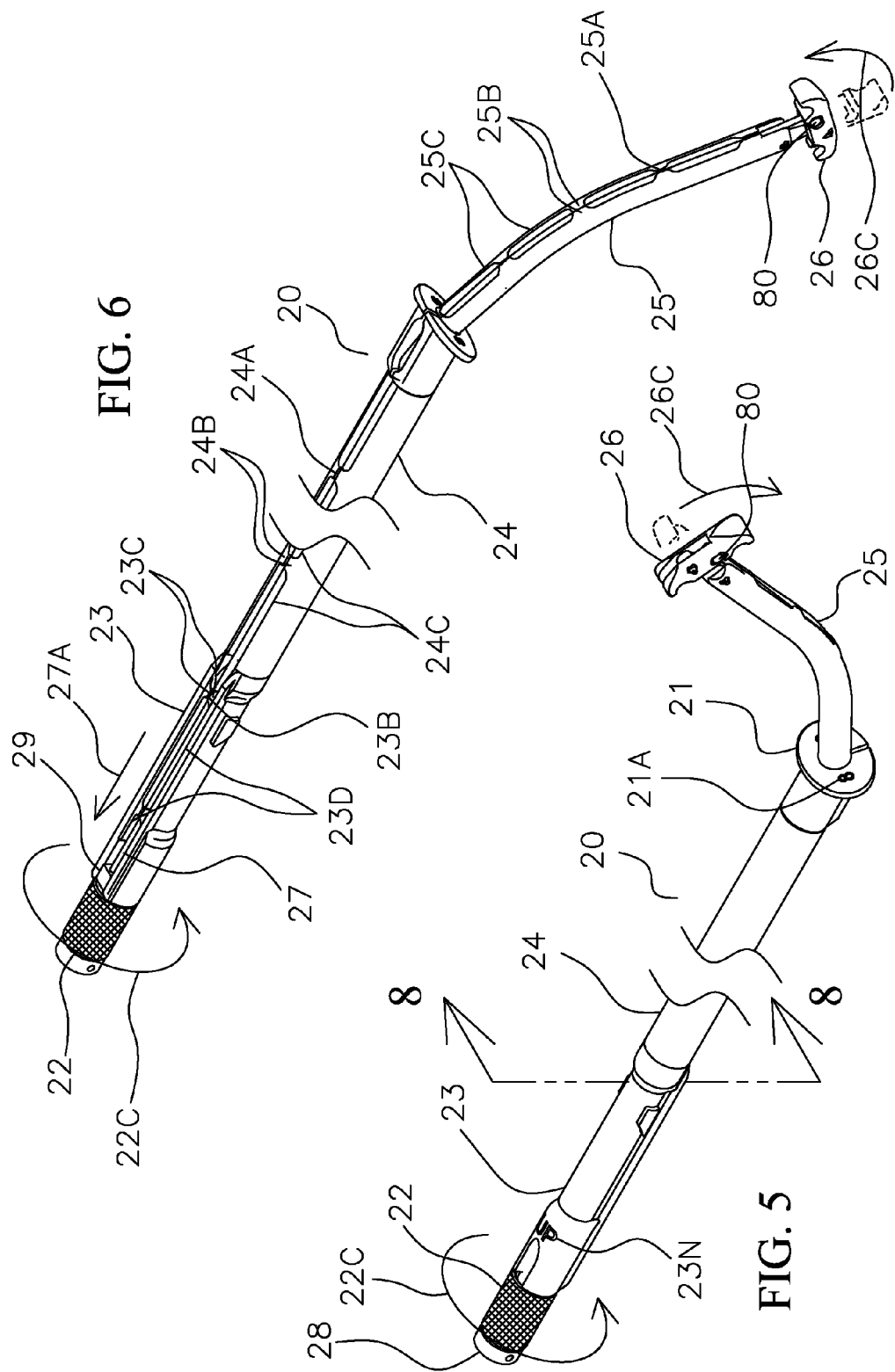

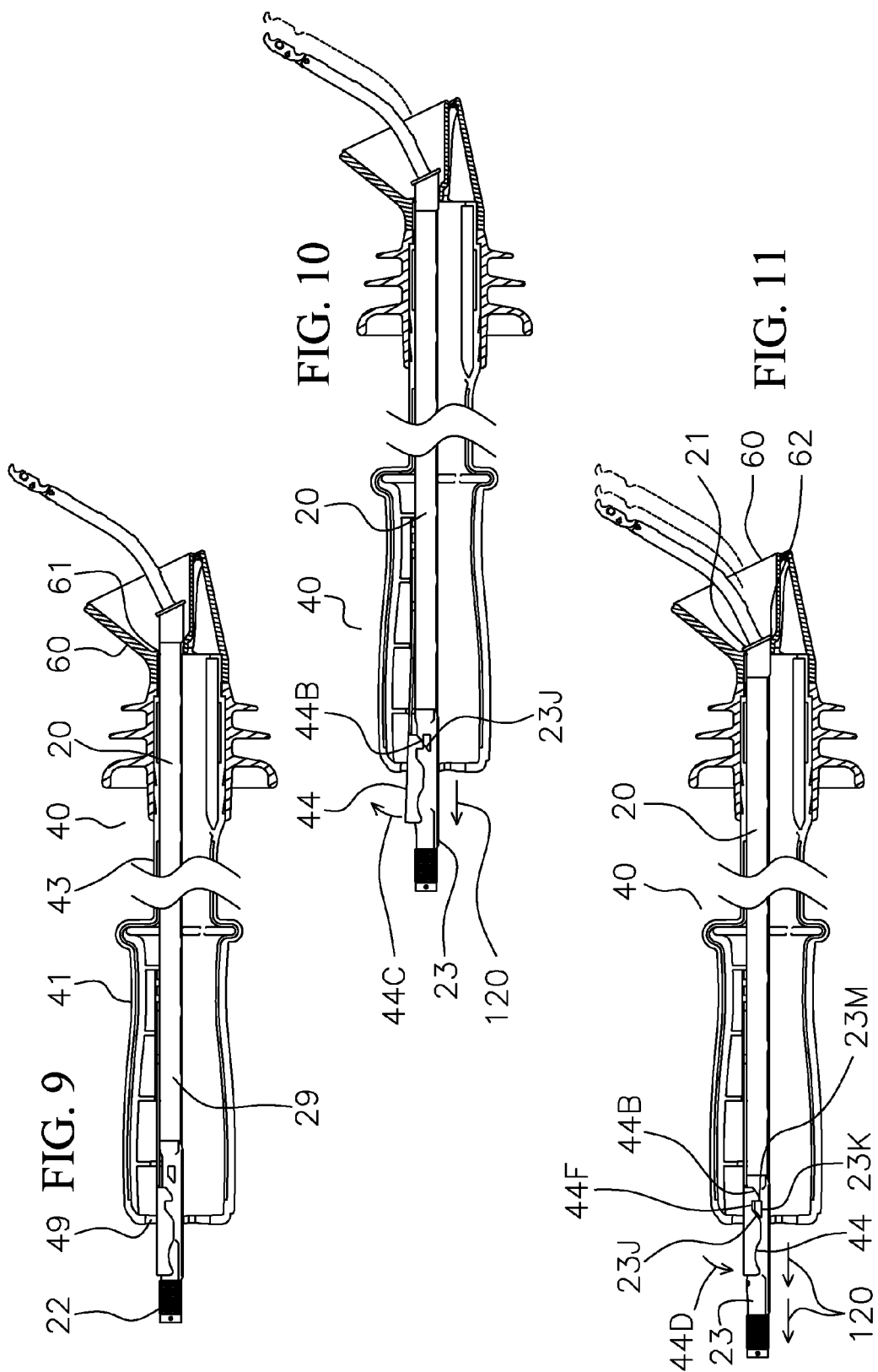

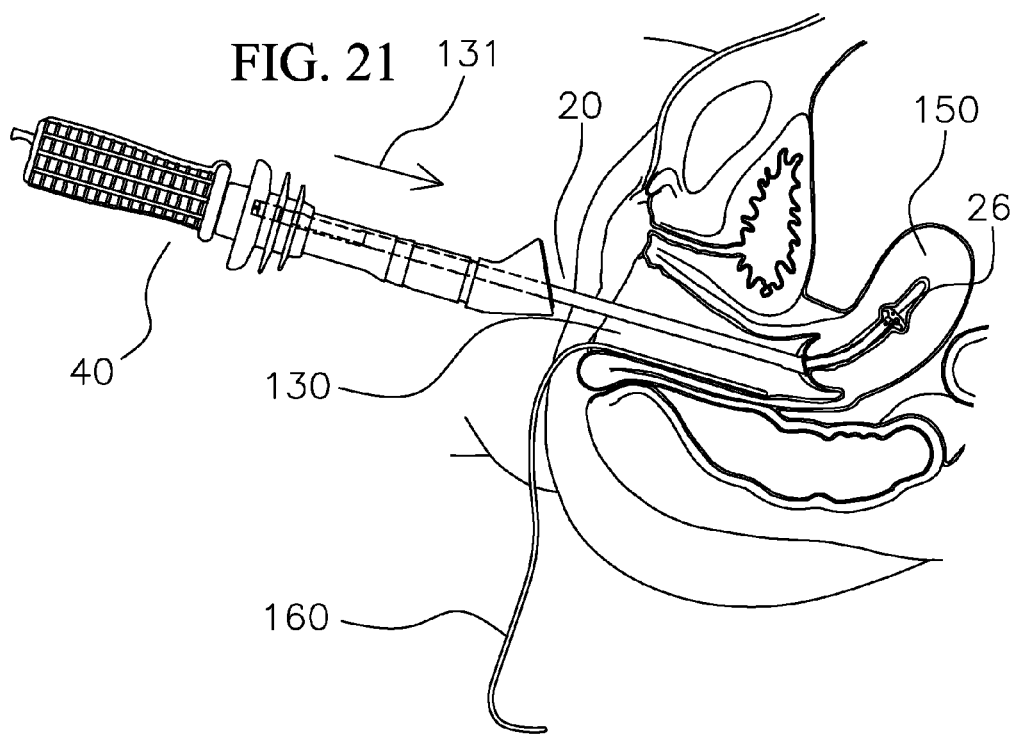
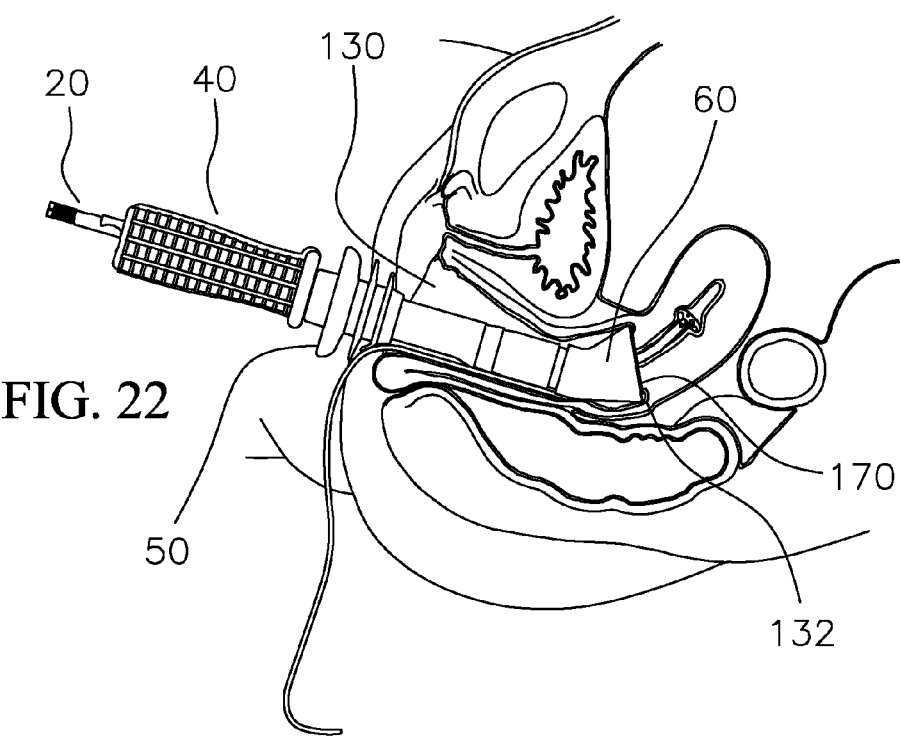

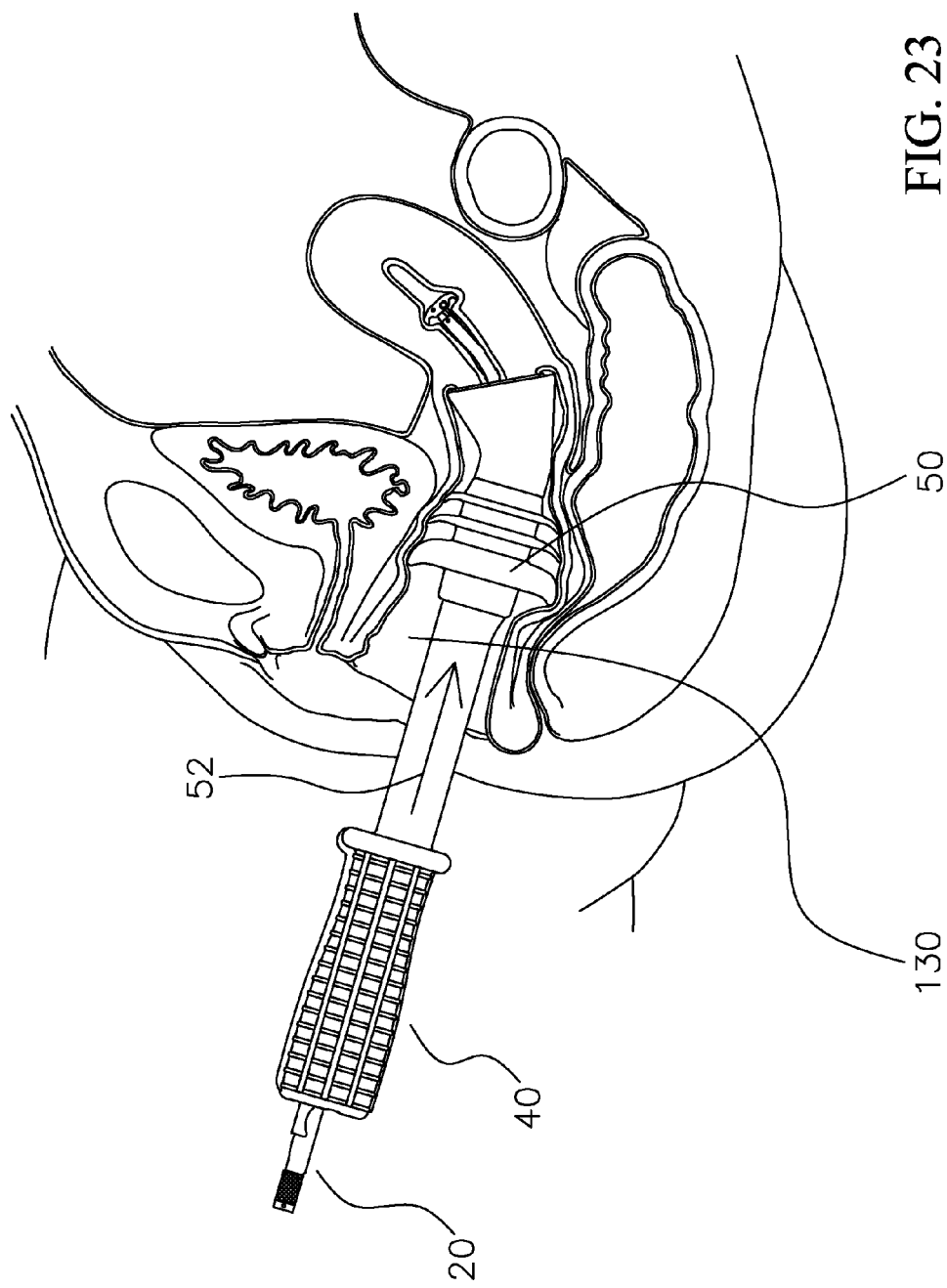

ERGONOMIC, LIGHTED UTERINE MANIPULATOR WITH CAUTERY

BACKGROUND OF THE INVENTION

Despite decades of commercial availability of a wide variety of transvaginally placed uterine manipulators, the need still exists for more effective and ergonomic surgical instruments to optimize the remote manipulation of a patient's vaginal, cervical and uterine tissues during modern minimally invasive gynecologic procedures. Naturally occurring openings in the body, like the vagina, urethra, anus and mouth, provide places to engage internal tissues without the requirement of cutting a hole in the patient's skin. Utilization of the vaginal canal to surgically access the cervix and uterus is routinely part of modern health care. As major gynecologic therapeutic interventions continue to become less invasive using fewer and smaller incisions, without better means for uterine control and mobilization, such procedures will become increasingly difficult to perform and require substantially more operative time, while potentially compromising patient safety and clinical outcomes. Extensive research has led to the invention and development of this new technology for uterine manipulation to address this critical unmet clinical need in women's health care.

DESCRIPTION OF RELATED ART

Surgeons have been placing medical implements through the vagina in efforts to treat gynecologic maladies for centuries. With the advent of sterile techniques, anesthesia and antibiotics, more advanced surgical interventions were developed. Initially a wide variety of generally cylindrical different size and shape devices, called sounds, were employed to explore and manipulate patients' vaginal canals, cervices and uteri.

Various purported proprietary product concepts have been developed over time. In 1976, for example, U.S. Pat. No. 3,948,270 described the use of a balloon to anchor a rigid tube within the uterine body to effect uterine fundal elevation and mobility while minimizing the hazard of uterine injury. This invention simply placed a balloon catheter over a rigid tube for insertion through the vagina and cervical canal into the body of the uterus for purposes of uterine injection. No means of engaging the cervix or uterus were provided.

U.S. Pat. No. 5,209,754 awarded in 1993, described a vaginal cervical retractor used to maneuver and visualize the uterus during surgical examinations and procedures. A balloon on a curved shaft is inserted into the uterine body to communicate with a plastic cup that engages the cervix within the forniceal region of the vagina. The cervical engaging cups were held in place by a hollow tube, which also provides a disc shaped barrier as a vaginal seal. This patent eventually led to the single-patient use, disposable Ahluwalia VCare® Uterine Manipulator product sold by ConMed Corporation (Utica, N.Y.).

In 1995, U.S. Pat. No. 5,394,863 described a pipe-like optical light guide with a hollow cup to transmit light through the vaginal fornices for surgical and medical procedures. While this invention recognized the utility of providing light to the fornices, it failed to provide a means to actively engage, pivot or manipulate the cervix and uterus. Further, it failed to provide an ergonomic handle to enable surgical control of the specimen. This patent appears to have never led to a commercially available product and the patent was prematurely abandoned. This patent cited eight predecessor patents (U.S. Pat. Nos. 4,449,519; 5,143,054; 5,131,380; 4,337,763; 4,597,383; 4,562,832; 3,945,371; 4,901,708) also involving surgical site illumination.

Subsequently, in 1996, 1997 and 1998, U.S. Pat. Nos. 5,520,698, 5,643,285 and 5,840,077, respectively, described methods and a uterine manipulation assembly for laparoscopic hysterectomy. This disclosure also provided a cup for cervical engagement located at the end of a hand-controlled device. Movement of this cup was achieved by the counter-intuitive side to side rotation of the proximal handle, which is perpendicular to the shaft of the device, leading to up and down movement of the distal cup. This means of moving the distal cup along with the attached cervix has proved to be surprisingly difficult for operating room staff routine implementation. Like the ConMed VCare® product, this technology also used a balloon within the uterine body to hold the device assembly onto the patient. An inflatable vaginal occluder on the shaft of the device assembly is described. This product concept, which uses both single-patient use disposable components and reusable components, led to the development of the KOH Colpotomizer™ used in conjunction with the RUMI® Uterine Manipulator as a product marketed and sold by CooperSurgical, Inc. (Trumbull, Conn.).

While several more uterine manipulators have been offered as commercial products or described in patent disclosures, they essentially involve non-ergonomic, counterintuitive handles (not co-linear with the device shaft) which function similarly to the RUMI® Manipulator. The ENDOPATH® Uterine Manipulator by Ethicon Endo-Surgery, Inc., (Cincinnati, Ohio) is a fully disposable hand-held device that offers a rotating handle perpendicular to the device shaft to move the distal cervical engagement element up and down through mechanical linkages. This complex plastic device is also secured by a balloon inflated in the uterine body. Other examples of completely reusable uterine manipulator products include the Marina Manipulator (Marina Medical, Sunrise, Fla.) and the Valtchev Manipulator (Conklin Surgical Instruments, Toronto, Canada). Alternative means for engaging the cervix and uterine body are described in European Patent Application # EP 2 116 202 A1 in which a threaded projection is screwed into the cervix and uterus to engage the cervical cup to the patient. Through limitations in effectiveness and ergonomics, none of these previous alternatives truly satisfy the requisite functionality of an optimized uterine manipulator for minimally invasive surgery.

BRIEF SUMMARY OF THE INVENTION

Briefly stated and in accordance with an embodiment of the invention, a uterine manipulator includes a sound and a body. The sound has a selectively actuatable anchor disposed proximate a distal end and an operating mechanism spaced from the anchor for controlling actuation of the anchor. The body has a passage therethrough adapted to receive the sound passed proximally through the body to a position in which the operating mechanism is accessible proximally of the body and the anchor extends distally.

In another embodiment, a uterine manipulator includes a generally straight, elongate body having a longitudinal axis and defining a substantially linear passageway therethrough, terminating at an opening in the cup; a handle on one end of the body having a longitudinal axis substantially co-axial with the longitudinal axis of the body; a cup on an opposite end of the body; and a sound having an elongate shaft receivable in the substantially linear passageway of the elongate body and a distal tip protruding from the opening in the cup. The cup has an opening angled relative to the longitudinal axis of the elongate body.

This novel product offers compelling effectiveness and ergonomic advantages over other similar pre-existing products. Gynecologic surgeons have repeatedly reported that remote uterine dissection, especially the vaginal cuff separation, remains a significant challenge despite multiple currently available products from other companies. Even with the availability and use of earlier uterine manipulator products, difficulties with cervical and uterine dissections are frequently associated with iatrogenic injuries to patients' bladders, ureters, vaginal vaults and surrounding tissues. Difficulties with this dissection often add substantial time to these operative procedures and are one of the leading causes of the need to convert laparoscopic procedures to more invasive open laparotomies.

The two main design goals for this invention were to develop a safe and truly effective technology for use under relevant surgical conditions, and then to provide a product that is easily learned and successfully deployed by surgeons and their assistants without requiring exhaustive training. The technology is designed to be more readily installed, intuitively obvious to position, and comfortable to hold. A compelling feature of this invention, to enable ease of installation, is the provision of an isolated slender customized sound which is readily installed through the cervix into the uterus. This compact sound acts as a guide over which the cervical engaging cup can be subsequently passed. The ability to install the sound alone readily enables its installation into the uterus under direct visualization within the vagina. This separate sound also makes its secure engagement to the uterus easy by turning the knurled knob to rotate the anchor. Since known alternative designs provide their uterine insertion elements already attached to the rest of their device, their distal insertion means is burdened with obstructing elements, such as their preinstalled balloons and cervical cups. Non-separated insertion features make device installation difficult to visualize and perform. The transvaginal installation of alternative products is significantly encumbered by having their devices' distal insertion components with unnecessary pre-attached larger diameter features. The provision of a physically separated engagement cup that slides over the installed sound makes the cervical cup installation fast and effective.

While many previous products reportedly can be used to surgically delineate the vaginal fornices and manipulate the uterus, this innovation simplifies and enhances critical anatomic identification and tissue mobilization in routine and complex minimally invasive gynecologic surgical interventions. This technology can become a cost-effective preferred means for surgeons striving to potentially improve patient outcomes and reduce procedure times.

This novel technology consists of four primary components, which are further provided in a variety of sizes to accommodate variations in patient anatomy. An ergonomic hand-held cervical engagement device with a custom co-axial handle at its proximal end is connected by an atraumatic shaft incorporating a sliding flexible vaginal occluder to an angled cup to receive the cervix at its distal end. Passageways within this cervical engagement device provide for receipt of additional components and features. To effectively engage and pivot the body of the uterus within the pelvis, an angled shaft (or sound) is provided to pass through the cervical engagement device, through the cervical canal and into the cavity in the body of the uterus, where a rotational anchor can be deployed to secure the shaft to the uterus. Additional options provided with this technology include the provision of light at the distal cervical cup to transilluminate and better visualize tissues of the vaginal fornix area and an energized dissection means to help dissect the uterus from the vagina.

A ridge on the handle of the cervical engagement device indicates the direction of the angled cervical cup and angled shaft of the sound. By simply rotating the handle, the cervical cup and angled sound rotate to pivot the uterus in the direction of the indicator ridge. When the indicator ridge is oriented up, the body of the uterus is pivoted up (i.e., ante flexed) to provide access for the posterior colpotomy (i.e., vaginal incision) dissection. When the ridge is down, the uterus is retroflexed to enable development of the bladder flap and anterior colpotomy; indicator ridge orientation to either side, enables ipsilateral uterine body pivoting for contra-lateral uterine blood vessel transillumination and dissection, along with colpotomy completion. When the indicator ridge orientation faces the patient's right side, the uterine body pivots towards the patient's right side, exposing the left side uterine arteries and veins (and potentially transilluminating them) and distracting these important blood vessels away from the left ureter. By creating further distance between these blood vessels and the adjacent ureter, this simple technique of rotating the coaxial handle to displace the uterus reduces the potential risk of ureteral injury during dissection. By rotating the indicator ridge to the opposite side, this same maneuver can expose the left uterine arteries, move them away from the left ureter and enable completion of the colpotomy.

For uterine manipulation during, for example, laparoscopic hysterectomy surgery, the components of this technology will have to be provided sterile to the operative field. The cervical engagement devices can be constructed of mostly common surgical plastics with different sized distal cervical cups. For example, distal cervical cups having inside diameters of 30, 35, or 40 mm could accommodate the range of cervical sizes most commonly encountered in hysterectomy surgery. The unique angled sounds offered in this invention can be reusable implements with customized angled shafts constructed of cleanable and resterilizable surgical quality metal; the distal ends of these sounds should have shaft diameters of 5 mm or less to readily pass through the cervical canal and be offered different lengths (e.g., commonly from 6 to 7 to 8 cm) to span the various lengths of patient's uterine bodies. A reusable, resterilizable metal and fiber optic vaginal illumination device can be employed or the illumination components can be integrated within the cervical engagement device. Likewise, the energy based dissection component can be reusable or single-use and integrated within the cervical engagement device.

In addition to a passageway for the angled sound, each cervical engagement device can also incorporate a passageway leading from its proximal end to a sealed transparent section in the distal cup. This passageway is parallel to the passageway for the angled sound and can be used to receive and secure a vaginal illumination device. This vaginal illuminator has a fan shaped, metal and fiber optic distal end, a shaft, and a proximal attachment feature. A standard threaded coupler is located at its proximal end to enable connection to a standard surgical light source. Light passes from the light source, through the light bundle, into the proximal end of the vaginal illuminator and out its distal end where it passes through the transparent section in the distal cervical cup.

The vaginal illuminator is an option that can be used at the surgeon's discretion with this technology for the provision of transillumination light delivered through the distal cervical cup. Using light to transilluminate or pass through targeted tissues is a common practice in minimally invasive surgery. Vaginal illumination is commonly employed in many routine gynecologic diagnostic and therapeutic interventions. When using commercially available alternative uterine manipulation products, it is frequently difficult to localize the vaginal fornices during laparoscopic hysterectomy. During this critical dissection, many very skilled and experienced surgeons have described the sense of getting lost deep in this pelvic anatomy. In accordance with an aspect of this invention, transillumination via the fiber optic vaginal illuminator through the transparent seal of the distal cervical cup can make identifying the cervical cup edges and the targeted fornices much easier. This transillumination technique may allow the surgical team to identify internal tissue structures, such as blood vessels, that lie within solid tissue planes. With this lighting option, important internal tissue elements can be differentiated through direct video imaging.

The resection or removal of the uterus requires the cervical region of the uterus to be dissected free or amputated from its attachments at the upper forniceal area of the vagina. This dissection is typically approached from one of two directions: "from below" or "from above." If the surgeon stands down between the patient's legs and passes dissecting instruments from outside towards the inside up through the vagina, as in a vaginal hysterectomy, this dissection is considered to be "from below." When dissecting is performed using the instruments placed "from above," the instruments are oriented in the preferred direction from the inside of the peritoneal cavity towards the vagina, as in traditional open surgery or in total laparoscopic hysterectomy, the surgeon can stay at the patient's side adjacent to the abdomen. By providing this new technology that also provides an energized dissection function, this unique approach facilitates the benefits and convenience of providing the dissection coming in from below along with the safety and ergonomics of viewing the dissection from the above, laparoscopic perspective. Thus, this technology provides for direct dissection of the vaginal cuff up through the vagina, while simultaneously viewing and performing laparoscopic surgery from above.

Extensive product development, including bench top and cadaver testing and related clinical evaluations, affirm the relative effectiveness, safety and durability of this new technology. The cervical engagement device with its angled sound along with the optional vaginal illuminator and integrated energized dissection features provide a compellingly improved alternative technology that has been favorably received by reviewing surgeons for enhanced uterine manipulation during minimally invasive gynecologic procedures.

BRIEF DESCRIPTION OF THE SEVERAL
VIEWS OF THE DRAWING(S)

While the novel aspects of the invention will be described with particularity in the appended claims, the invention itself together with further objects and advantages thereof may be more readily understood by reference to the following detailed description of the presently preferred embodiments of the invention taken in conjunction with the accompanying drawing in which:

FIG. 2A is a rear perspective view of the device subsystem of FIG. 2

FIG. 3 is an orthogonal cross sectional view along lines 3-3 of the instrument of FIG. 1;

FIG. 4 is an exploded perspective view of a device subsystem of the invention of FIG. 1 illustrating the components and assembly of said subsystem;

FIG. 5 is an overhead perspective view of a sound subsystem of the preferred embodiment of the instrument of FIG. 1;

FIG. 6 is an underside perspective view of the sound subsystem presented in FIG. 5;

FIG. 9 is an orthogonal cross sectional view along lines 3-3 of the instrument presented in FIG. 1 demonstrating the introduction of the sound subsystem first detailed in FIG. 5 into the distal end of the device subsystem of FIG. 4;

FIG. 10 is again an orthogonal cross sectional view along lines 3-3 of the instrument presented in FIG. 1 demonstrating the progression, first initiated in FIG. 9, of the sound subsystem into the device subsystem;

FIG. 11 is yet again an orthogonal sectional view along lines 3-3 of the instrument presented in FIG. 1 detailing the final stage of integration, advanced from FIG. 10, of the sound subsystem into the device subsystem;

FIG. 21 is, again, an anatomical sagittal view illustrating the device subsystem of FIG. 4 being manipulated and positioned onto the sound subsystem of FIG. 5 and advanced into a vaginal canal;

FIG. 22 is, again, an anatomical sagittal view showing the device and sound subsystems shown in FIG. 21 fully integrated wherein an occluder is approaching the vaginal opening and the device subsystem is contacting vaginal fornices;

FIG. 23 is an anatomical sagittal view showing the device of FIG. 4 wherein the occluder is fully advanced into the vaginal canal;

DETAILED DESCRIPTION OF THE INVENTION

While the invention has been described in connection with certain presently preferred embodiments thereof, those skilled in the art will recognize that many modifications and changes may be made without departing from the broad scope of the invention, which is intended to be defined solely by the appended claims.

Figure 1:
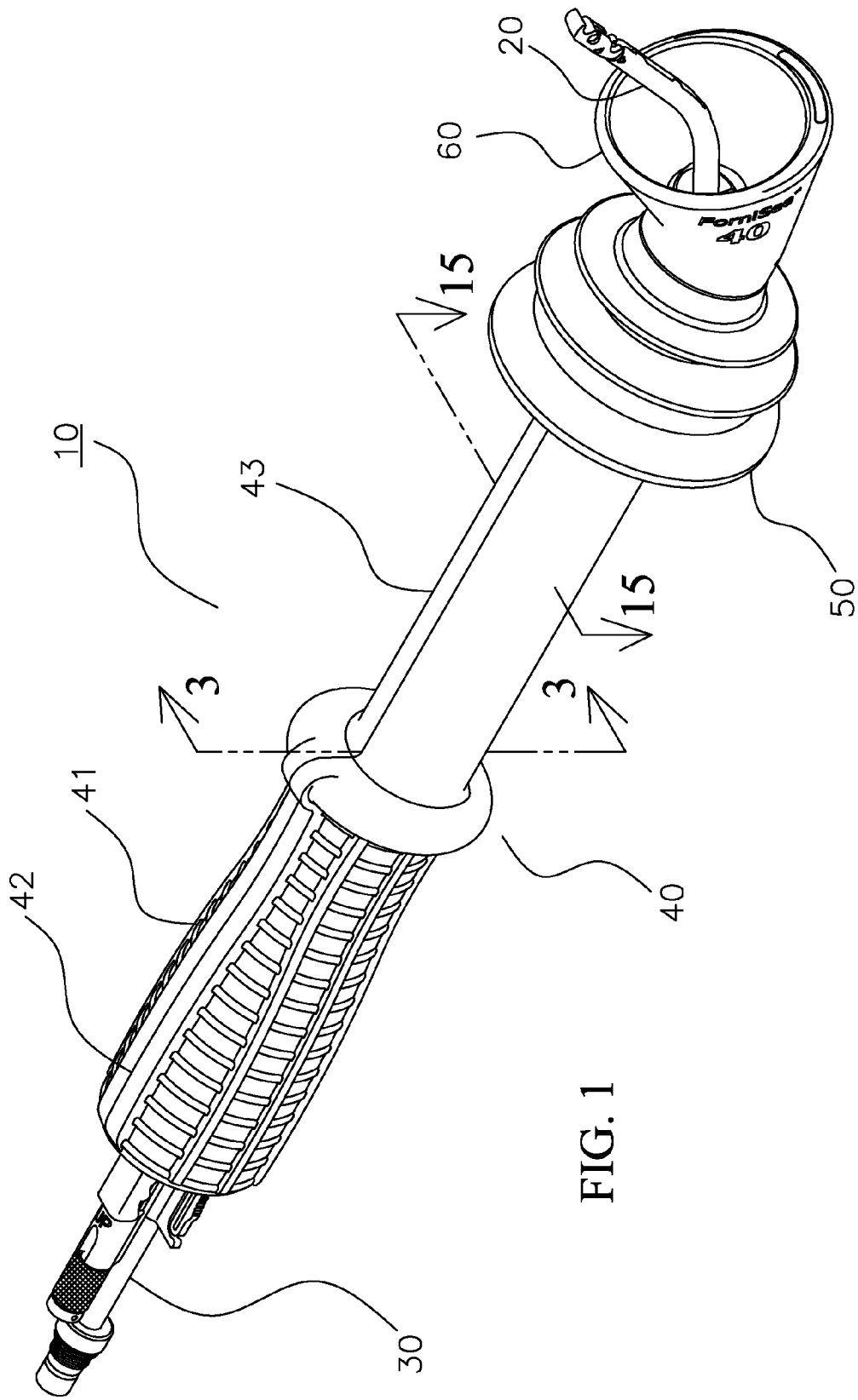
FIG. 1 is a perspective view of an instrument in accordance with an aspect of the invention as presented for use.

Referring to FIG. 1, a perspective view of a uterine manipulator 10 is shown, comprised of a sound 20 and a light wand 30 accepted within and housed by a device 40. The sound 20 and light wand 30 are generally manufactured such that they are reusable and preferably comprised of rigid, sterilizable, and cleanable materials such as stainless steels and the like. The device 40 is typically disposable and generally comprised of sterilizable molded polymers.

Evident in the device 40 are a proximally located textured handle 41 imparting a tactile surface for ease of physical manipulation of manipulator 10 and device 40, an indicator ridge 42 to delineate manipulator 10 orientation within a surgical field, a centrally situated shaft or body 43 providing support to and visual indication of insertion depth for the manipulator 10, a distally positioned occluder 50 to maintain intra-peritoneal gas pressure within the surgical field, and a distally sited cup 60 for cervical engagement.

Figure 2:
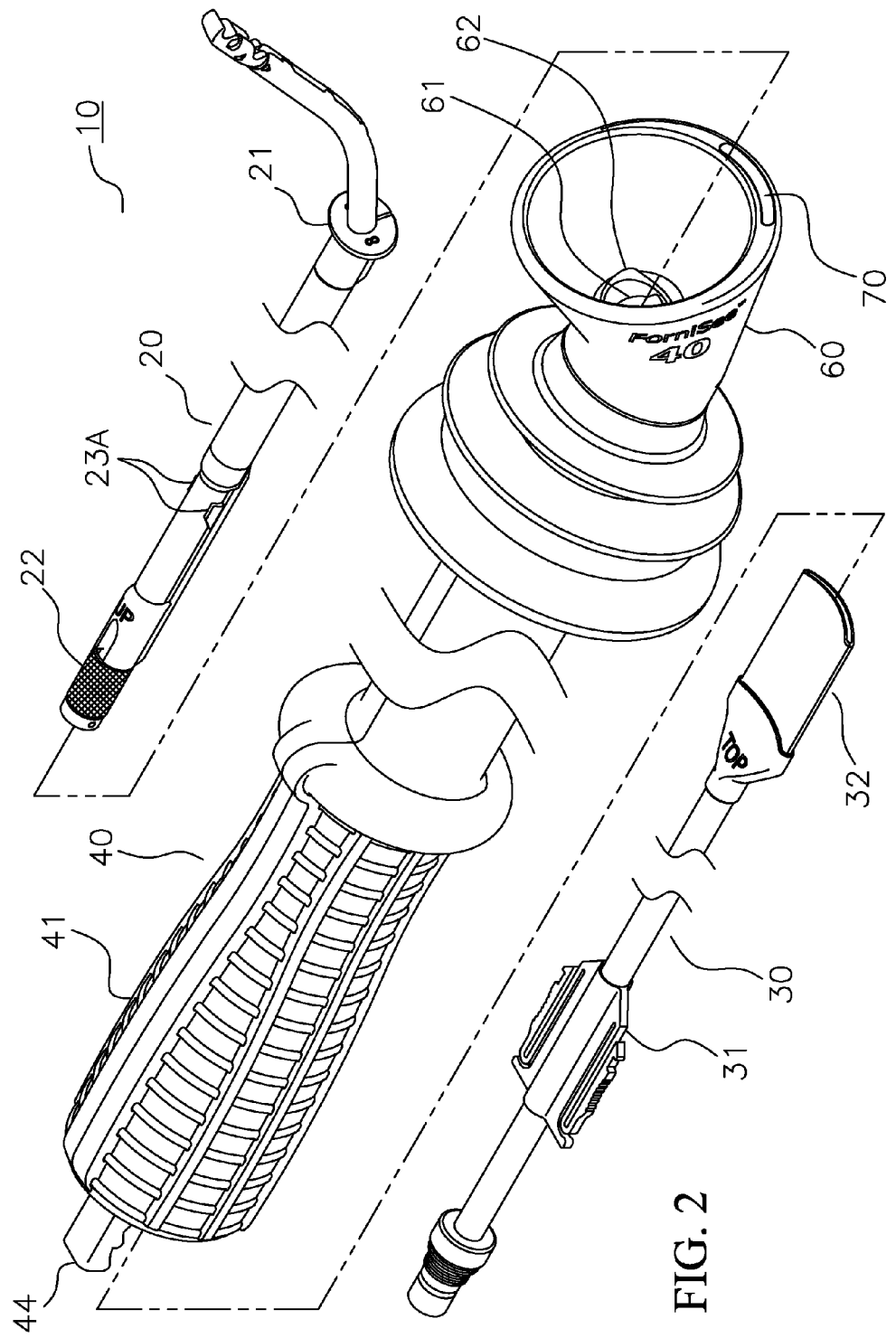
FIG. 2 is an exploded perspective view of the instrument of FIG. 1 illustrating the subsystems of the preferred embodiment.

FIG. 2 shows an exploded perspective view of the uterine manipulator 10 with the sound 20 and light wand 30 removed from the device 40. The sound 20 is received through the distal end of the device 40 while the light wand 30 is received through the proximal end of the device 40.

The sound 20 is inserted distally through a sound port 61, which is a substantially linear passageway formed through the device body, such that a cervical stop 21 rests firmly against a stop ledge 62 provided in the cup 60. When inserted fully into the sound port 61, an anchor nut 22 protrudes from textured handle 41 as opposed wedge stops 23a engage with a latch 44.

The light wand 30 is insertable proximally into the device 40 through a wand port 45, in the textured handle 41, best shown in FIG. 2A, until a winged snap 31 engages with receiving edges 46 of the wand port 45. A wand fan 32 mates adjacent to a window 70 within the cup 60.

FIG. 2A is a proximal view of the device 40 and highlights a latch port 49 through which the latch 44 and the sound 20 subsystem shown in FIG. 2 protrude from the textured handle 41 and the wand port 45 through which the light wand 30 is introduced and engages with receiving edges 46.

FIG. 3 is an orthogonal section view taken along sectioned lines 3-3 of the uterine manipulator 10 of FIG. 1 showing the positions of the assembled sound 20 and light wand 30 within the device 40. In the illustrated orientation, the sound 20 is located vertically above the light wand 30. The cervical stop 21 of the sound 20 is engaged with the stop ledge 62 in the cup 60 and the wand fan 32 is nested adjacent to the window 70 within the cup 60.

Shown in FIG. 4 is an exploded perspective view of the device 40. The device 40 is purposefully meant to be supplied as a sterile, one-time use product. A left handle 47 and a right handle 48 are assembled to capture tabs 44a of the latch 44 within left receptacles 47A of the left handle 47 and symmetrically opposed right receptacles (not shown) of the right handle 48. The left handle 47 and right handle 48 are typically made from an opaque medical grade plastic and produced from an injection molding process and assembled and retained via a mechanical force fit, ultrasonic welding process, or adhesives. The latch 44 is preferably made from a formed stainless steel sheet, but can be made from a resilient medical grade polymer.

The occluder 50 is slid over the shaft 43 such that a bore 51 of the occluder 50 engages with ridges 43a of the device 40 and creates an airtight seal around the shaft 43. In an embodiment, the occluder 50 can be slid back and forth and positioned along the shaft 43 as dictated by the surgical procedure. The occluder 50 is made of a transparent or translucent molded flexible polymer such as medical-grade silicone.

The window 70 is disposed in the cup 60 such that a front face 71 of the window 70 is flush with a distal face 63 of the cup 60. The joint between the cup 60 and window 70 is preferably hermetic to prevent the introduction of bodily fluids in proximity to the heat intense areas of a wand fan 32 of the light wand 30, and can be accomplished via mechanical press fits, gasketing, or adhesive fillers. The window 70 is produced via injection molding processes and is made of a heat resistant transparent material such as polyetherimide (commercially available from GE Plastics under the trade name Ultem®) or from other high performance transparent acrylics. The cup 60 is similarly made from an injection molded, but opaque heat resistant plastic such as Ultem®. The device 40 can be manufactured and offered with a variety of cups 60 to accommodate a variety of cervical sizes. For convenience in identification, the respective cups 60 may be marked with the appropriate nomenclature via a marking 65 provided on the cup 60.

The assembled cup 60 with window 70 are inserted over a head 43b of the body 43 such that the window 70 is positioned coplanar with, but opposite from, the indicator ridge 42 of the device 40. The cup 60 is preferably fixedly and permanently attached to the shaft 43 during a surgical procedure, for example, via a mechanical force fit or with the aid of adhesives.

Referring to FIGS. 5 through 8, the sound 20, a subsystem of the uterine manipulator 10, is detailed. The sound 20, as described, is preferably meant to be supplied as a sterile, cleanable, and reusable product that is used to probe and couple to the uterine structures. Additional operational characteristics of the sound 20 are explained below.

FIG. 5 is an overhead perspective view of the sound 20 initially detailed in FIG. 2. The sound 20 is centrally comprised of a substantially cylindrical keyed shaft 24, which distally supports an angled shaft 25 and a rotational anchor 26. A guide shaft 23, and anchor nut 22, and a cap 28 are disposed proximally on the sound 20. It should be noted that due to variations in the human anatomy, different sizes of devices may be required from one surgical case to the next. The sound 20 can be manufactured and offered with a variety of angled shafts 25 to accommodate the array of anatomical differences. For convenience in identification, the respective angled shafts 25 may be marked with the appropriate nomenclature via a marking 21A provided on the cervical stop 21. Additionally, to aid in orientation of the insertion of the sound 20 into device 40 and provide for verification of the orientation of the rotational anchor 26, a marking 23N may be applied to the guide shaft 23.

A clockwise rotation 22C of the anchor nut 22, as viewed from the anchor nut 22 end of the sound 20, will cause a drive screw 29 and attached drive wire 27, more readily viewed in FIG. 6, to retract and induce a pulling force on an anchor barrel 80 housed within rotational anchor 26. This pulling will cause the rotational anchor 26 to follow rotation direction 26C, pivoting about a pivot point, and move perpendicular to the angled shaft 25. Conversely rotating the anchor nut 22 in the opposite direction will impart a pushing force on the anchor barrel 80, causing the rotational anchor 26 to return to its original position aligned with the angled shaft 25.

FIG. 6 is an underside perspective view of the sound 20 of FIG. 5. From this perspective, proximally, the drive screw 29 is shown. As described above, the drive screw 29 is engaged with the anchor nut 22 to push or pull the drive wire 27 which engages with and directs the rotational anchor 26. The drive wire 27 emanating from the drive screw 29 is delivered through the guide shaft 23 via a wire channel 23B, retained by retaining tabs 23C and allowed cleaning access via cleaning troughs 23D. The wire 27 also passes through the keyed shaft 24 via a wire channel 24A, where it is retained by retaining tabs 24B and allowed cleaning access via cleaning troughs 24c. Lastly, the wire also passes through the angled shaft 25 via a wire channel 25A, where it is retained by retaining tabs 25B and allowed cleaning access via cleaning troughs 25C. At the distal end of the wire channel 25A, the wire 27 connects to the rotational anchor 26. Again, a clockwise rotation 22C of the anchor nut 22, as viewed from the anchor nut 22 end of the sound 20, will cause the drive screw 29 and its attached drive wire 27 to retract in pull direction 27A and induce a pulling force on the anchor barrel 80 housed within rotational anchor 26 and cause the rotational anchor 26 to follow rotation direction 26c and move perpendicular to the angled shaft 25. Conversely rotating the anchor nut 22 in the opposite direction will return the rotational anchor 26 to its original position parallel to the angled shaft 25. Of course, using a reverse threaded anchor nut 22 could provide for opposite actuation between the perpendicular and aligned positions.

Figure 7:
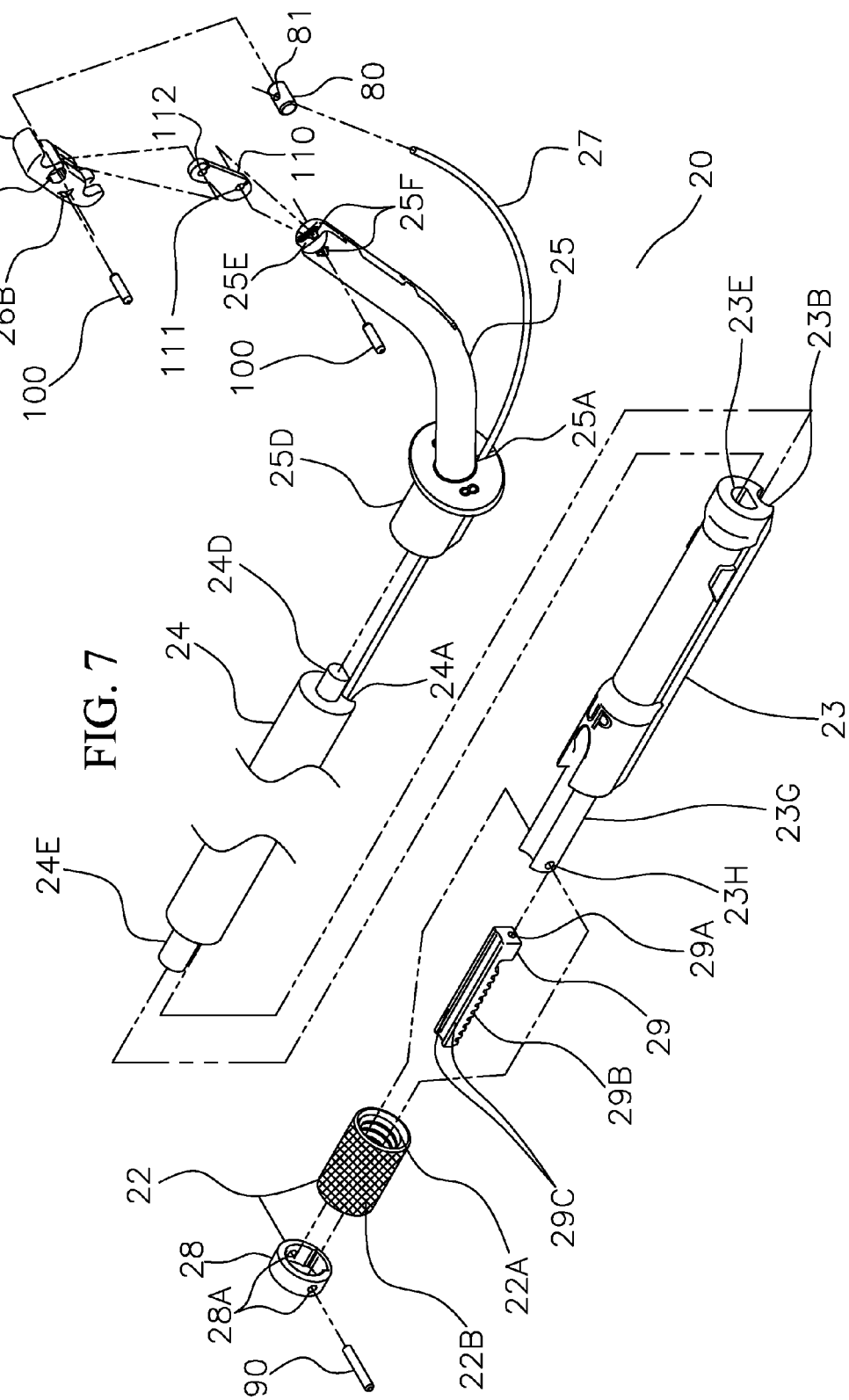
FIG. 7 is an exploded perspective view of the sound subsystem presented in FIG. 5 illustrating the components and assembly of said subsystem.

FIG. 7 is an exploded perspective view of the sound 20 of FIG. 5 wherein the components and assembly order are detailed. The keyed shaft 24 preferably is manufactured from a rigid sterilizable material, such as stainless steel, and is connected to the angled shaft 25 via a distal boss 24D which is inserted into a receptacle housing 25D. The angled shaft 25 preferably is also of a non-corrosive, biocompatible material similar to the keyed shaft 24. The assembled keyed shaft 24 and angled shaft 25 are further assembled to the guide shaft 23 wherein a proximal boss 24E is retained in a receiving bore 23E. The guide shaft 23 is also favorably selected from similar non-corrosive, biocompatible material. In a preferred embodiment, the keyed shaft 24, angled shaft 25, and the guide shaft 23 are permanently joined to form a unitary boss, e.g., via a welding or brazing process, although they may be coupled via other means.

The drive wire 27 is a common non-corrosive, biocompatible material such as stainless steel wire and is inserted into a wire bore 29a of the drive screw 29 and permanently attached via welding or brazing. The drive screw is typically made from a commercial stainless steel with a common industrial thread 29b.

Figure 8:
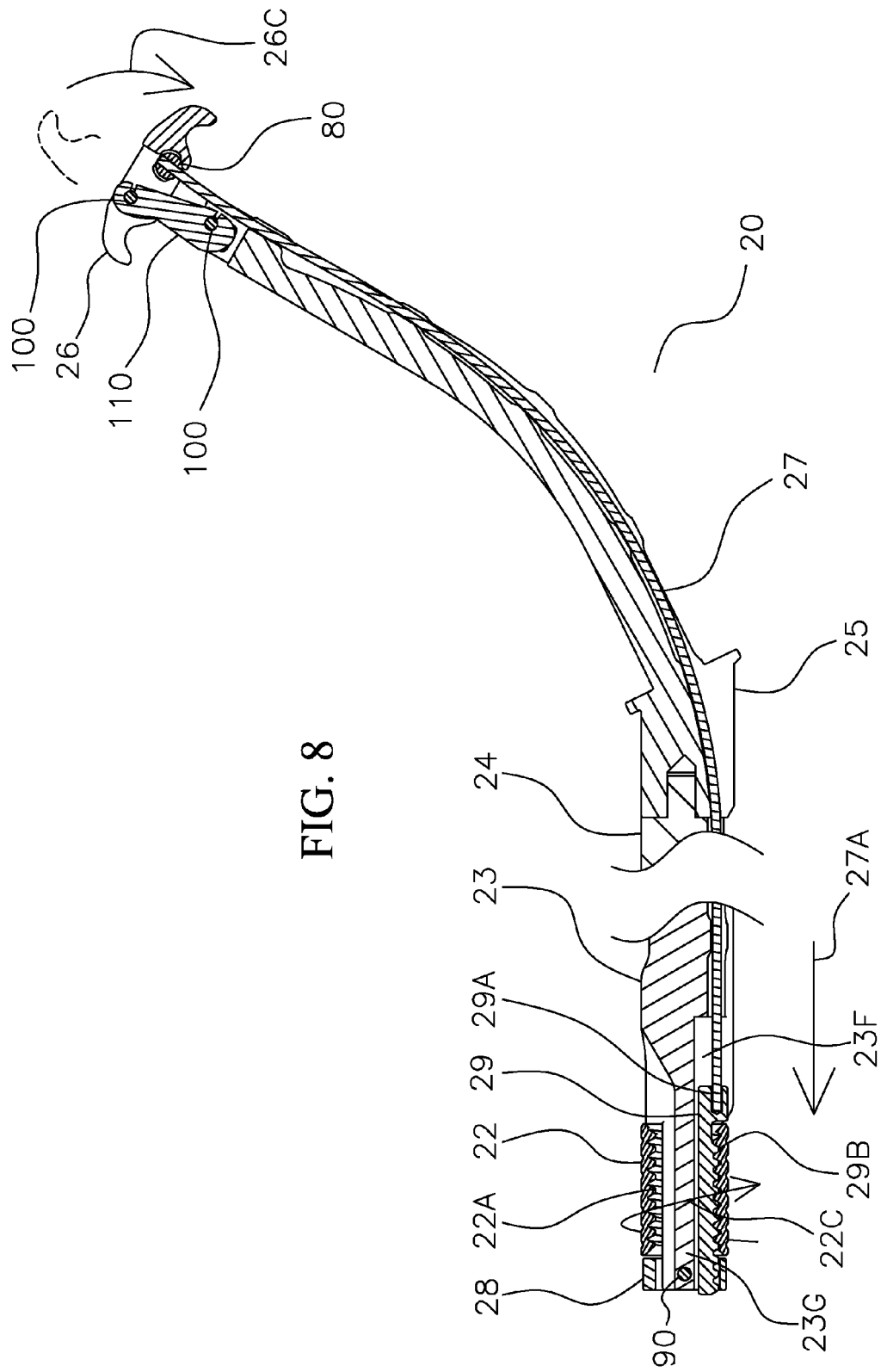
FIG. 8 is an orthogonal cross sectional view along lines 8-8 of the sound subsystem presented in FIG. 5 illustrating the components and operational characteristics of said subsystem.

The assembled drive wire 27 and drive screw 29 are delivered through the previously assembled guide shaft 23, keyed shaft 24, angled shaft 25 by communicating the drive wire 27 through the wire channel 23B, wire channel 24A, and wire channel 25A, correspondingly, such that a guide surface 29C of the drive screw 29 is in contact with a drive channel 23F, more effectively conveyed in FIG. 8, of the guide shaft 23. The anchor nut 22, which also can be made from a commercial, non-corrosive, biocompatible material such as stainless steel, contains an internal thread 22A that mates with thread 29B of drive screw 29 and external knurling 22B to aid in digital manipulation in typical wet, slippery surgical cases. The anchor nut 22 is threaded onto the drive screw 29, over a retaining shaft 23G of the guide shaft 23 and secured with the cap 28 by inserting a cap pin 90 through a pin bore 28A in the cap 28 and through a subsequent pin bore 23H in the proximal end of the retaining shaft 23G of the guide shaft 23. The cap 28 and cap pin 90 may be of a commercial, non-corrosive, biocompatible material such as stainless steel.

The free end of the drive wire 27 is passed through a wire hole 81 in the anchor barrel 80 and secured flush via welding or brazing. The anchor barrel 80, which can be made from stainless steel and is in all aspects similar to a common dowel pin, protrudes from the angled shaft 25 in proximity to a link receptacle 25E. The anchor barrel 80 is guided into a barrel bore 26A of rotational anchor 26 such that the anchor barrel 80 rests central to the rotational anchor 26.

A dowel pin 100 is pressed into and through a dowel bore 25F of the angled shaft and through a shaft bore 111 of an anchor link 110 waiting in the link receptacle 25E of the angled shaft 25. The anchor link 110 is typically fabricated from a rigid material such as stainless steel and provides a means to allow the rotational anchor 26 to pivot while remaining attached to the angled shaft 25. A link bore 26b of the rotational anchor 26 is positioned concentric to an anchor bore 112 of the anchor link 110 and a dowel pin 100 is pressed through to retain the rotational anchor 26 while still allowing rotation.

FIG. 8 is an orthogonal cross sectional view of the sound 20 taken along lines 8-8 of FIG. 5 further illustrating the sound 20. As described above, the rotational anchor 26 is held by both the anchor barrel 80, which is fixedly attached to the drive wire 27, and the anchor link 110, which is secured by the dowel pin 100, relative to the angled shaft 25. The anchor link 110 is secured to the angled shaft by the dowel pin 100. The angled shaft 25 is oriented and secured to the keyed shaft 24 which is subsequently oriented and secured to the guide shaft 23, which houses the drive screw 29 in the drive channel 23F. The thread 29B of the drive screw 29 mates with the internal thread 22A of the anchor nut 22 and is secured to the retaining shaft 23G of the guide shaft 23 via the cap pin 90 which is pressed through the cap 28 and subsequently through the guide shaft 23. The drive wire 27 is fed through the angled shaft 25, the keyed shaft 24, and the guide shaft 23 and securely fastened within the wire bore 29A of the drive screw 29. Again, as arranged in the Figures, clockwise rotation 22C of the anchor nut 22, as viewed from the anchor nut 22 end of the sound 20, will cause the drive screw 29 and its attached drive wire 27 to retract in pull direction 27A and induce a pulling force on the anchor barrel 80 housed within rotational anchor 26 to cause the rotational anchor 26 to follow rotation direction 26C and move perpendicular to the angled shaft 25. Conversely rotating the anchor nut 22 in the opposite direction will return the rotational anchor 26 to its original position aligned with the angled shaft 25.

In reference to FIGS. 9 through 11, the steps of engaging the sound 20 within the device 40 are detailed. The sound 20 distally enters the device 40 through the cup 60, transits the shaft 43 via a passageway in the shaft, engaging the latch 44, and exits the textured handle 41.

FIG. 9 shows the sound 20 as it enters the device 40 through the sound port 61 of the cup 60. The keyed shaft 24 is housed within the shaft 43 and the anchor nut 22 protrudes from the textured handle 41 via the latch port 49.

FIG. 10 illustrates the insertion progression of the sound 20 through the device 40 wherein the sound is advanced in direction 120 such that the activation wedge 23J of the guide shaft 23 engages the ramp 44B forcing the latch 44 to flex in direction 44C providing physical resistance and subsequent tactile feedback of sound 20 engagement with the latch 44 of device 40.

FIG. 11 illustrates the next sequence of advancing the sound 20 through the device 40. Therein the sound 20 has further advanced through the device 40 in direction 120 such that, distally, the cervical stop 21 of the sound 20 rests firmly against stop ledge 62 in the cup 60, and proximally, the activation wedge 23J of the guide shaft 23 has cleared the ramp 44B of the latch 44. The latch 44 returns to its normal position through direction 44D and latch catch 23K rests within latch recess 44E such that a shaft stop 23M interfaces with a sound stop 44F, physically locking the sound 20 within the device 40. In this position, inadvertent decoupling of the subsystems while in use is prevented. Removal of the sound 20 from the device 40 is accomplished by simply lifting the latch 44 to disengage the latch 44 by allowing the latch recess 44E to clear the latch catch 23K so that sound 20 may be extracted from the distal end of device 40.

Figure 12:
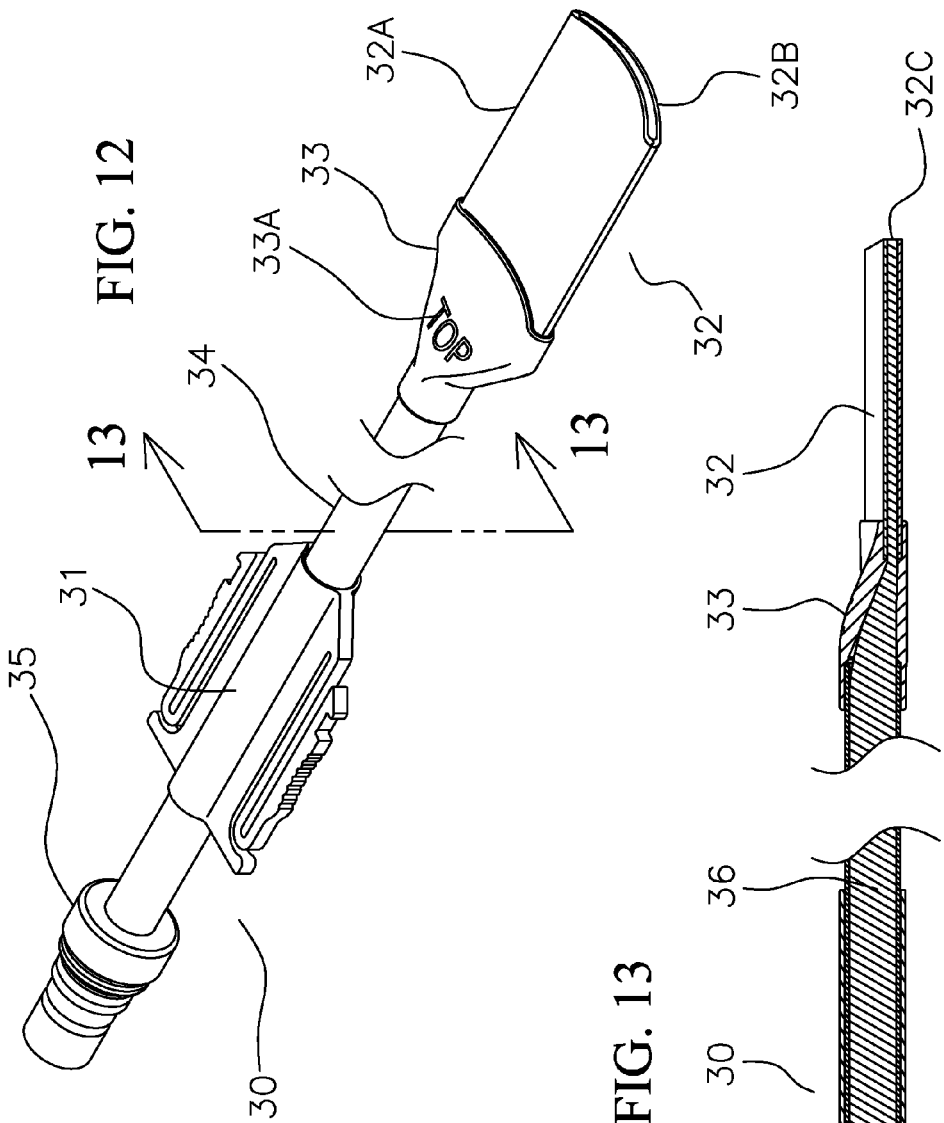
FIG. 12 is a perspective view of a light wand subsystem of the preferred embodiment of the instrument of FIG. 1.
Figure 13:
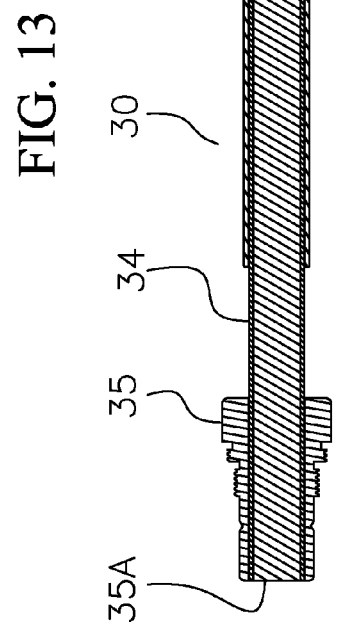
FIG. 13 is an orthogonal cross sectional view taken along lines 13-13 of FIG. 12 illustrating the components and assembly of said subsystem.
Figure 14:
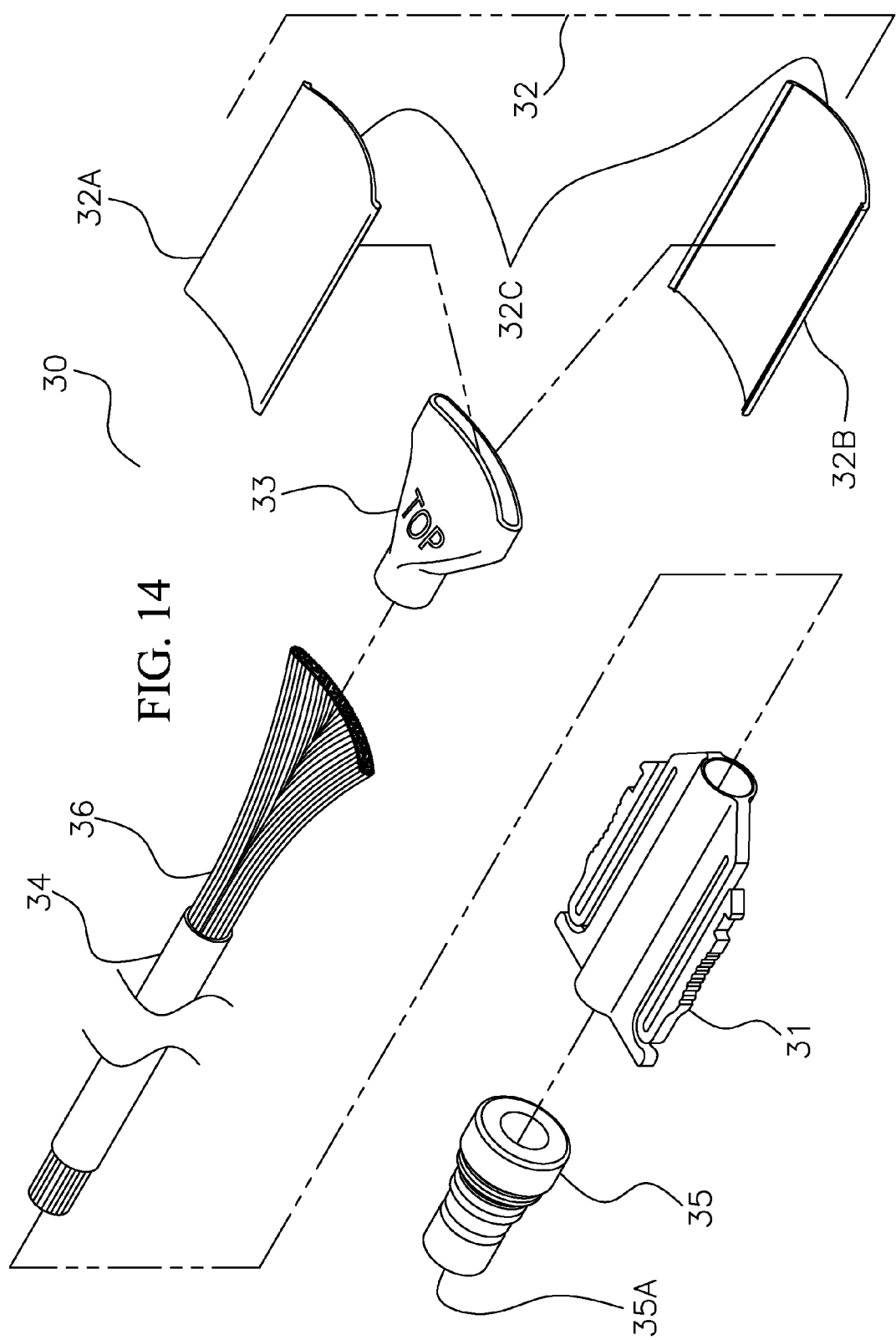
FIG. 14 is an exploded perspective view of the light wand subsystem presented in FIG. 12 illustrating the components and assembly of said subsystem.

The light wand 30 subsystem is detailed in FIGS. 12 through 14. Generally, the light wand 30 is used to transilluminate the vaginal fornices during dissection to help visualize the internal structure of the area being dissected. Vascular structures are highlighted with the use of the light wand 30 and can help the surgeon choose satisfactory areas to perform the dissection to reduce bleeding. In one embodiment, the light wand 30 is intended to be a rigid, cleanable, and reusable component that is selectively received in and removed from the device 40. It preferably is made from robust sterilizable materials like medical grade stainless steels. In other embodiments, the light wand 30 may be fixed in the device 40.

FIG. 12 is a perspective view of the light wand 30 detailing the components used in the assembly of said subsystem. Distally oriented to the subsystem is the wand fan 32, comprised of an upper half 32A and a lower half 32B, which are coupled to the fan coupler 33. When, as in the illustrated embodiment, the light wand is selectively received in and removable from the device, the fan coupler 33 or any other component of the light wand 30 may be permanently inscribed with a marking 33A to provide the surgeon a visual cue to aid in the insertion of the light wand 30 into the device 40. A wand shaft 34 is connected to the fan coupler 33, and a winged snap 31 is attached over the wand shaft 34 in a majoritively proximal location. An input adapter 35 is attached proximally to the wand shaft and is used to provide a mating thread for attachment to many commercially available fiber optic light sources such as a Karl Storz Xenon 300 manufactured by Karl Storz GmbH & Co. KG, Tuttlingen, Germany.

FIG. 13 is an orthogonal section view taken along lines 13-13 of FIG. 12 further indicating the component structure of the light wand 30. As illustrated, an optical bundle 36 is centrally housed within the wand shaft 34. The proximal end of the bundle mates flush with an input face 35A of the input adapter 35. The bundle funnels through the fan coupler 33 and the distal end is flush with an exit face 32C of the wand fan 32.

FIG. 14 is an exploded perspective view of the light wand 30 that illustrates the components and assembly of said subsystem. Distally oriented to the subsystem is the wand fan 32, comprised of the upper half 32A and the lower half 32B, which are coupled to the fan coupler 33 for example, via a welding, brazing, or adhesive process. The upper half 32A and lower half 32B of wand fan 32 and the fan coupler are typically manufactured from a rigid biocompatible material such as stainless steel or the like. The fan coupler 33 is fixedly joined to a similarly biocompatible wand shaft 34, preferably by a welding, brazing or adhesive process. Proximally, a winged snap 31 is fixed to the wand shaft 34, preferably by a welding, brazing or adhesive process. The input adapter 35, preferably made from stainless steel, is fixed to the proximal end of the wand shaft 34 and completes the external structure of the light wand 30 subsystem.

The optical bundle 36 is packed within the wand shaft 34, and made flush with the input face 35A of the input adapter 35 and the exit face 32C of the wand fan 32. The optical bundle 36 is most typically comprised of a group of tightly packed optical fibers that are polished at each end to maintain optical efficiency and prevent light loss. The optical bundle 36 may be secured within the light wand 30 using optical adhesives.

Figure 15:
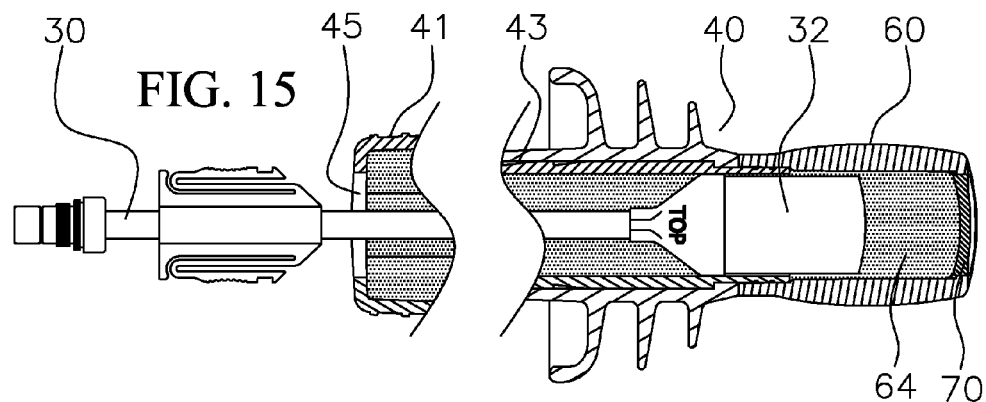
FIG. 15 is an orthogonal cross sectional view along lines 15-15 of the instrument presented in FIG. 1 demonstrating the introduction of the light wand subsystem first detailed in FIG. 12 into the proximal end of the device subsystem of FIG. 4.
Figure 16:
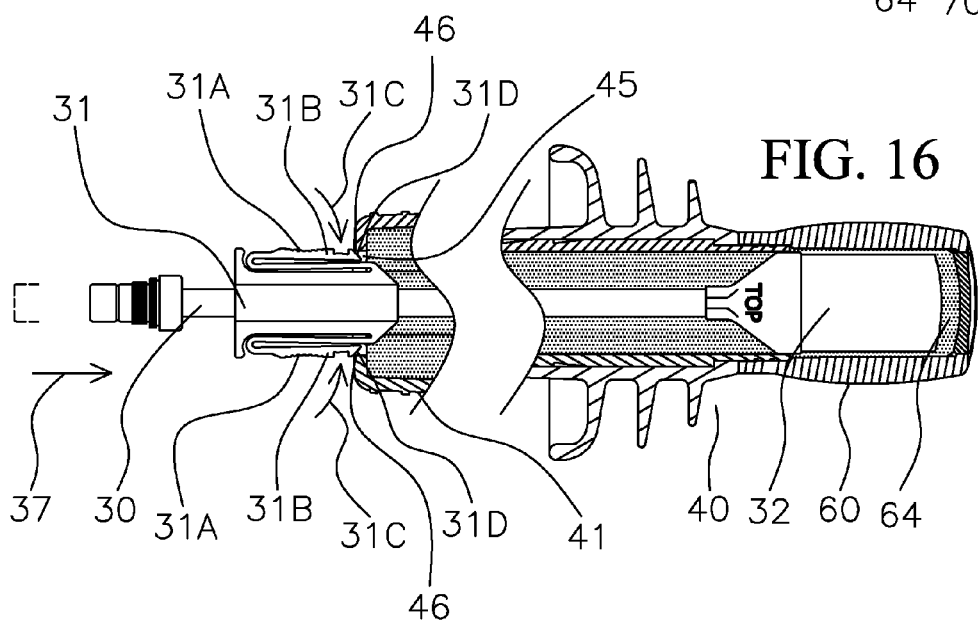
FIG. 16 is again an orthogonal cross sectional view along lines 15-15 of the instrument presented in FIG. 1 demonstrating the progression, first initiated in FIG. 15, of the light wand subsystem into the device subsystem.
Figure 17:
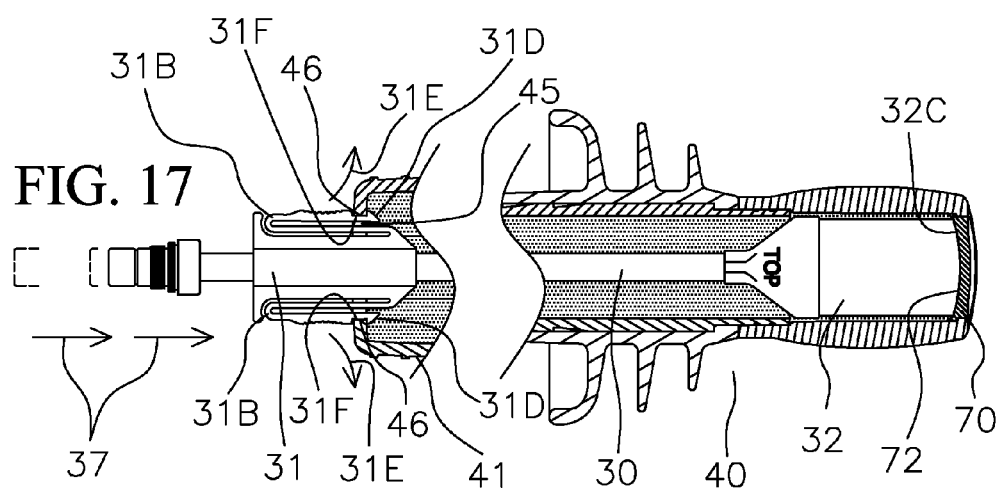
FIG. 17 is yet again an orthogonal sectional view along lines 15-15 of the invention presented in FIG. 1 detailing the final stage of integration, advanced from FIG. 16, of the sound subsystem into the device subsystem.

FIGS. 15 through 17 are orthogonal section views taken along lines 15-15 of FIG. 1 and are useful to detail the introduction of the light wand 30 subsystem into the device 40 subsystem. For clarity, the sound 20 subsystem is not shown. The light wand 30 is intended to pass through the device 40 and rest in proximity to the window 70 of the cup 60 such that optical efficiency is maintained and light loss is avoided as light emitted from the exit face 32C passes through the window.

In FIG. 15, the light wand 30 has been introduced wand fan 32-first into the wand port 45, which is a passageway extending through the device 40, along direction 37 shown in FIG. 16, such that the wand fan 32 is disposed in the fan cavity 64 of the cup 60.

In a successive step illustrated in FIG. 16, the light wand 30 progresses further into the device 40 via direction 37 until the winged snap 31 interfaces with the receiving edges 46 of the wand port 45. By forcing the light wand 30 into the wand port 45, or by depressing finger grooves 31A, spring arms 31B compress in direction 31C allowing ramp tips 31D to engage with the receiving edges 46 and further compress the spring arms 31B to allow the winged snap 31 access into the wand port 45.

FIG. 17 shows that continued insertion of the light wand 30 into the device 40 causes the wand fan 32 to stop against the window 70 such that the exit face 32C of the wand fan 32 is adjacent to, and preferably in intimate contact with, a rear face 72 of the window 70. The exit face 32C's contact with, or adjacency to, the rear face 72 ensures maximum light transmissivity and minimizes optical losses. Also in this position, the ramp tips 31D clear the receiving edges 46 of the wand port 45 allowing the spring arms 31B to return to their normal position through direction 31E and subsequently capturing the winged snap 31 within the wand port 45 by the nesting of receiving troughs 31F inside the receiving edges 46 of the wand port 45. The light wand 30 is retained in the device 40 until the spring arms 31B are compressed to unlatch the receiving troughs 31F from the receiving edges 46.

FIGS. 18 through 24 employ a variety of orthogonal anatomical views, also known as sagittal views, and enlarged detail views, to highlight the preferred use of the uterine manipulation system 10 in a surgical field. The uterine manipulation device 10 is used to provide support for, retention of, and dissection assistance with processes associated with hysterectomies.

Figure 18:
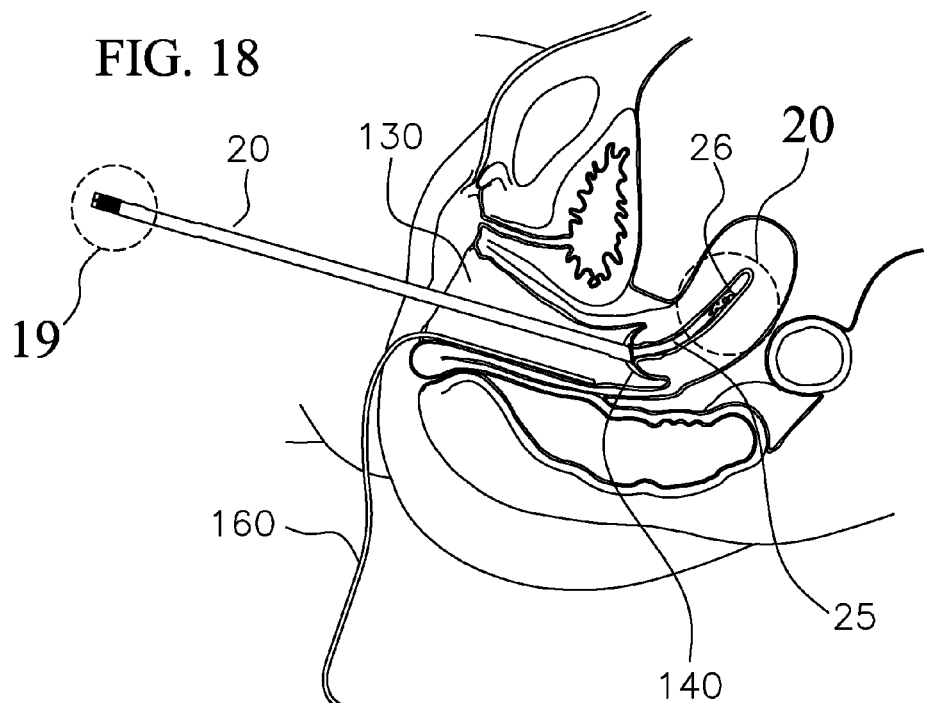
FIG. 18 is an orthogonal side view of the human anatomy taken along the midline, also known as a sagittal view, showing the sound subsystem of FIG. 5, as presented in its preferred method of intravaginal use, passing first through a cervix and into a uterus.

FIG. 18 is an orthogonal, midline anatomical view, also known as a sagittal view, showing a retractor 160 maintaining an opening and line of sight into a vaginal canal 130. As illustrated, the sound 20 is inserted through the vaginal canal 130 such that the cervical stop 21 rests against an external cervical os 140 and the angled shaft 25 enters the uterus 150. The sound 20 is used to probe the cervix and retain the uterus 150 for removal after a uterine dissection. The rotational anchor 26 described above is actuated to its perpendicular position to serve these purposes. Although the invention utilizes the novel rotational anchor 26 illustrated and described previously, other anchors could be used. Any selectively actuatable device that can be readily inserted into the uterus and then expanded, including a conventional device, may be used.

Figure 19:
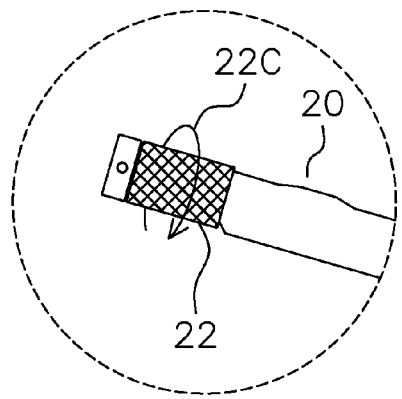
FIG. 19 is an enlarged detail view of the proximal end of the sound subsystem shown in FIG. 18 illustrating the operation of said subsystem in the preferred method of use.
Figure 20:
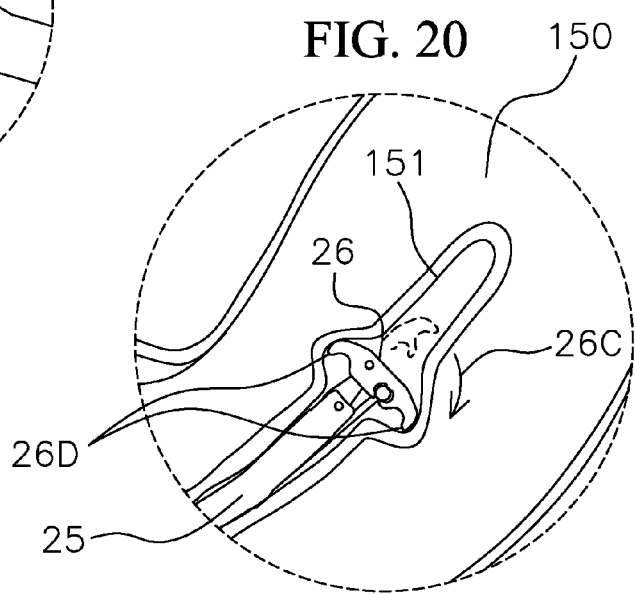
FIG. 20 is an enlarged detail view of the distal end of the sound subsystem shown in FIG. 18 illustrating the operation of said subsystem in the preferred method of use.

FIG. 19 is an enlarged detail view of the proximal end of FIG. 18 showing the method of engagement of the sound 20. Specifically, the anchor nut 22 is moved in a clockwise rotation 22C, as viewed from proximal end, while the orientation of the sound 20 is maintained in relation to the anatomy. The result of this rotation is shown in FIG. 20. More specifically, FIG. 20 shows that the rotational anchor 26 is moved in the rotation direction 26C such that the rotational anchor 26 is deployed and anchor fingers 26D engage the endometrial lining 151 of the uterus 150. The anchor nut 22 activated in FIG. 19 deploys the rotational anchor 26 such that it is, for the most part, perpendicular to the angled shaft 25. In this perpendicular position, the rotational anchor 26 with the anchor fingers 26D, the uterus is held securely and readily extracted when desired. Likewise, rotating the anchor nut 22 in a counterclockwise direction will return the rotational anchor 26 to its original position parallel to the angled shaft 25 and allow for the ready release of the extricated uterine tissue.

FIG. 21 shows the sound 20 in position such that the actuated rotational anchor 26 is nested in the uterus 150. Also in this Figure, the device 40 is introduced into the vaginal canal along direction 131 with the sound disposed in the sound port. The retractor 160 may be used as a guide to aid in insertion of the device 40.

FIG. 22 is a sagittal view depicting the device 40 further inserted into the vaginal canal 130 until the cup 60 meets and envelops the cervix 170, resting in the vaginal fornix 132.

FIG. 23 is yet another sagittal view showing the device 40 fully connected with the sound 20. Also in this Figure, the occluder 50 is advanced into the vaginal canal 130 in direction 52 so as to seal the vaginal canal 130 to maintain intraperitoneum pressure.

Figure 23A:
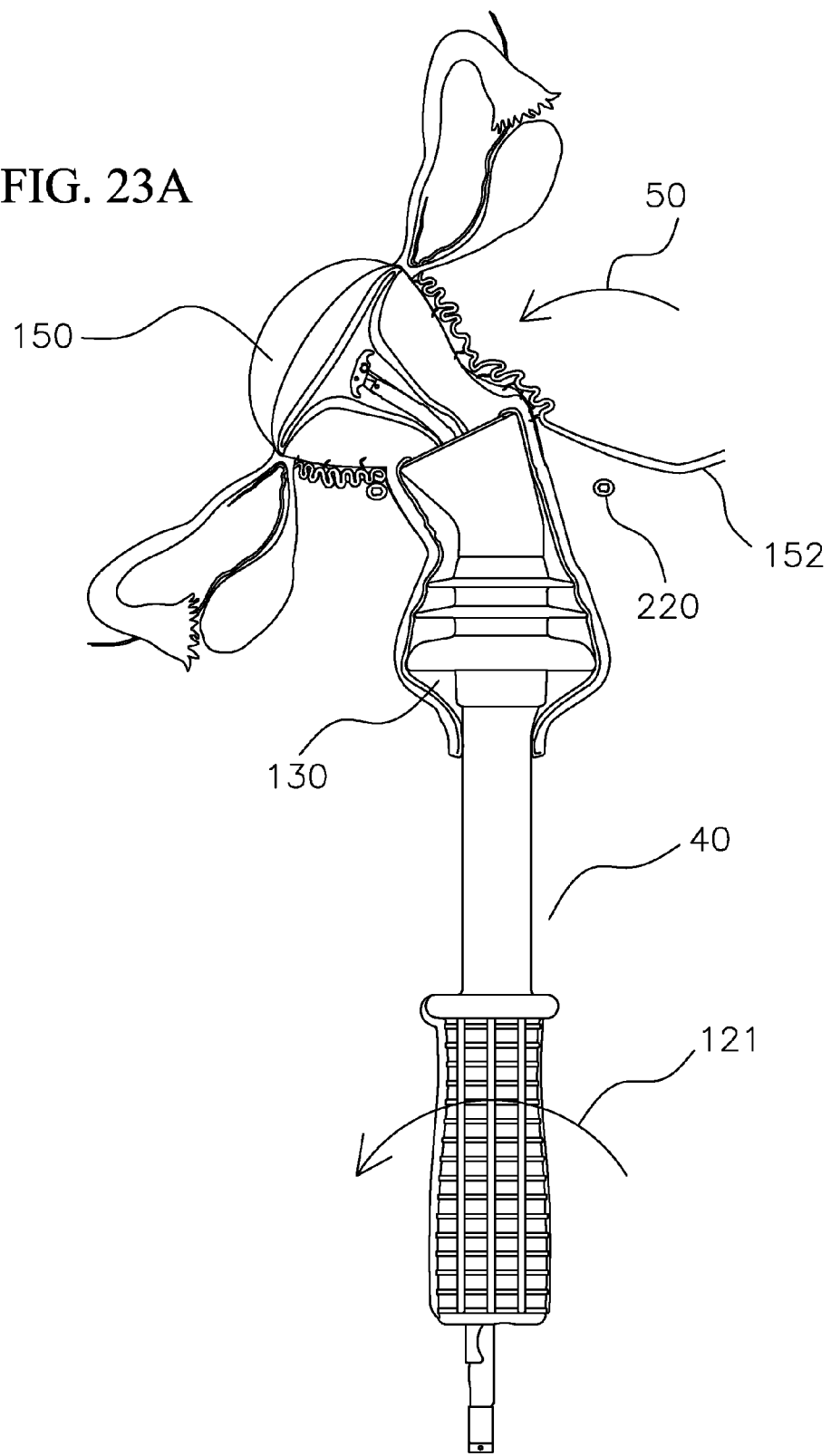
FIG. 23A is an orthogonal section view of the human anatomy taken along the front, also known as an anterior or coronal view, illustrating the rotation of the device within the vaginal canal and the subsequent displacement of the uterus relative to the surrounding anatomy to distance the uterine artery from the ureter.

FIG. 23A is a frontal anatomical section, or a coronal view, illustrating the rotation of the device 40 along direction 121, i.e., about the longitudinal axis of the device 40, within the vaginal canal 130. Because the cup 60 contacting the cervix 170 is angled relative to the longitudinal axis of the device, such rotation imparts a right lateral displacement 153 of the uterus 150 (from the patient's perspective) creating a margin of safety between a left ureter 220, and a left uterine artery 152 in preparation for a left lateral colpotomy. Rotating device 40 in the opposite direction would consequently provide for a left lateral displacement of the uterus 150 (from the patient's perspective) a right lateral colpotomy.

Figure 24:
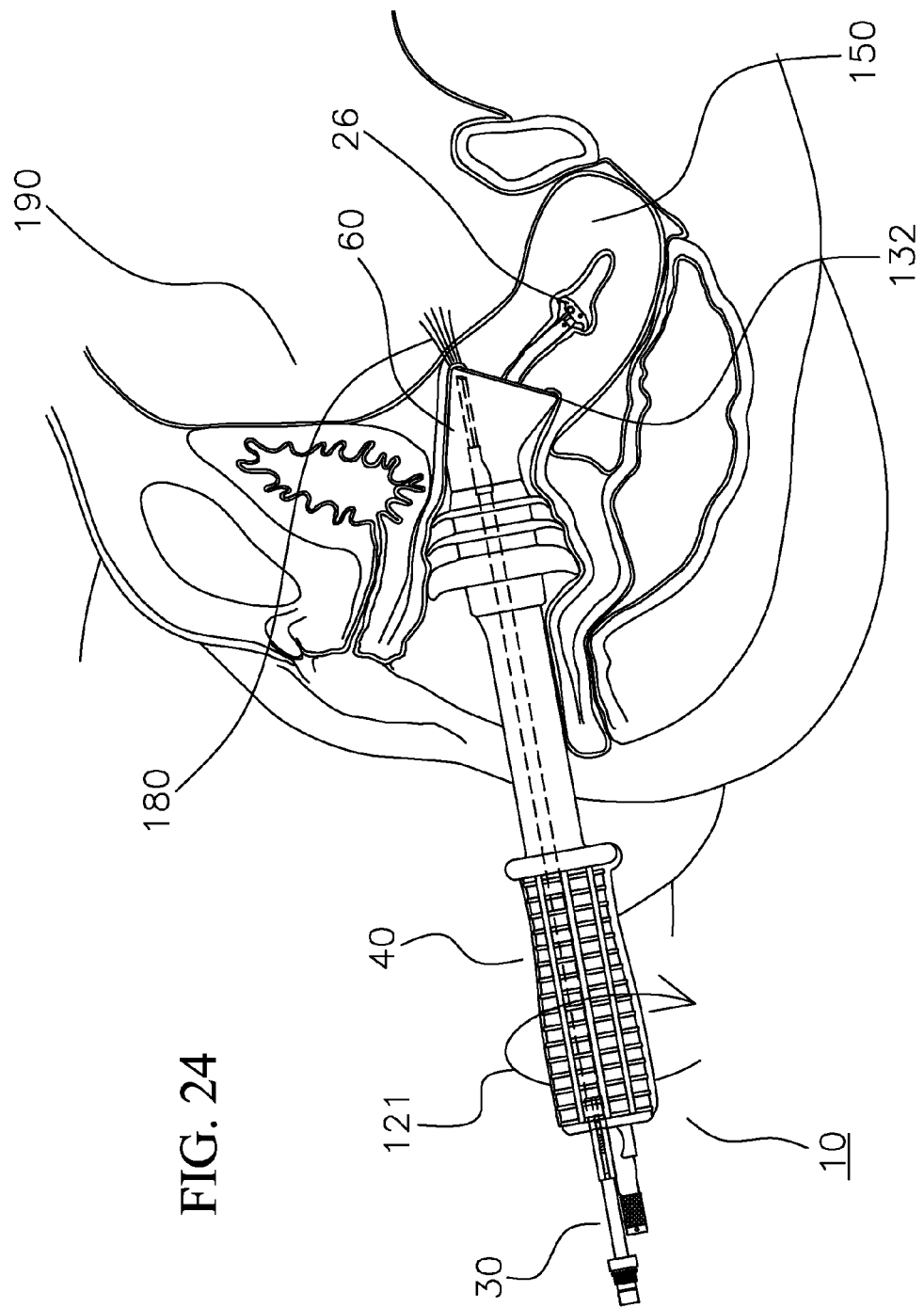
FIG. 24 is an anatomical sagittal view illustrating the system of FIG. 1 fully emplaced within the field of surgical use such that the light wand of FIG. 12 is introduced proximally through the device of FIG. 4 and introducing light through the vaginal fornices.

FIG. 24 is a sagittal view wherein the device 40 has been rotated substantially 180-degrees in direction 121, i.e., about the longitudinal axis of the device 40, to reposition the uterus 150 in retroflexion. In this position, additional surfaces of the uterus are readily accessible to a surgeon. As should be appreciated from FIGS. 23A and 24, the uterine manipulator 10 of the present invention allows for repositioning of the uterus 150 in any desirable position through rotation about a single axis, which is the longitudinal axis of the device. During rotation, a positive pressure is maintained between the cup 160 and the uterus 150, but the cup 60 will rotate relative to the uterus 150. The sound 20 also will rotate relative to the uterus 150, as it is fixed relative to the cup 60. The rotational anchor 26 preferably has smooth surfaces, to facilitate this relative movement and prevent injury within the uterus 150.

FIG. 24 also illustrates the incorporation of the light wand 30 into the device 40. Light 180 is passed through the system via the light wand 30 to illuminate the vaginal fornix 132 through the abdominal cavity 190 to aid in the colpotomy.

Figure 25:
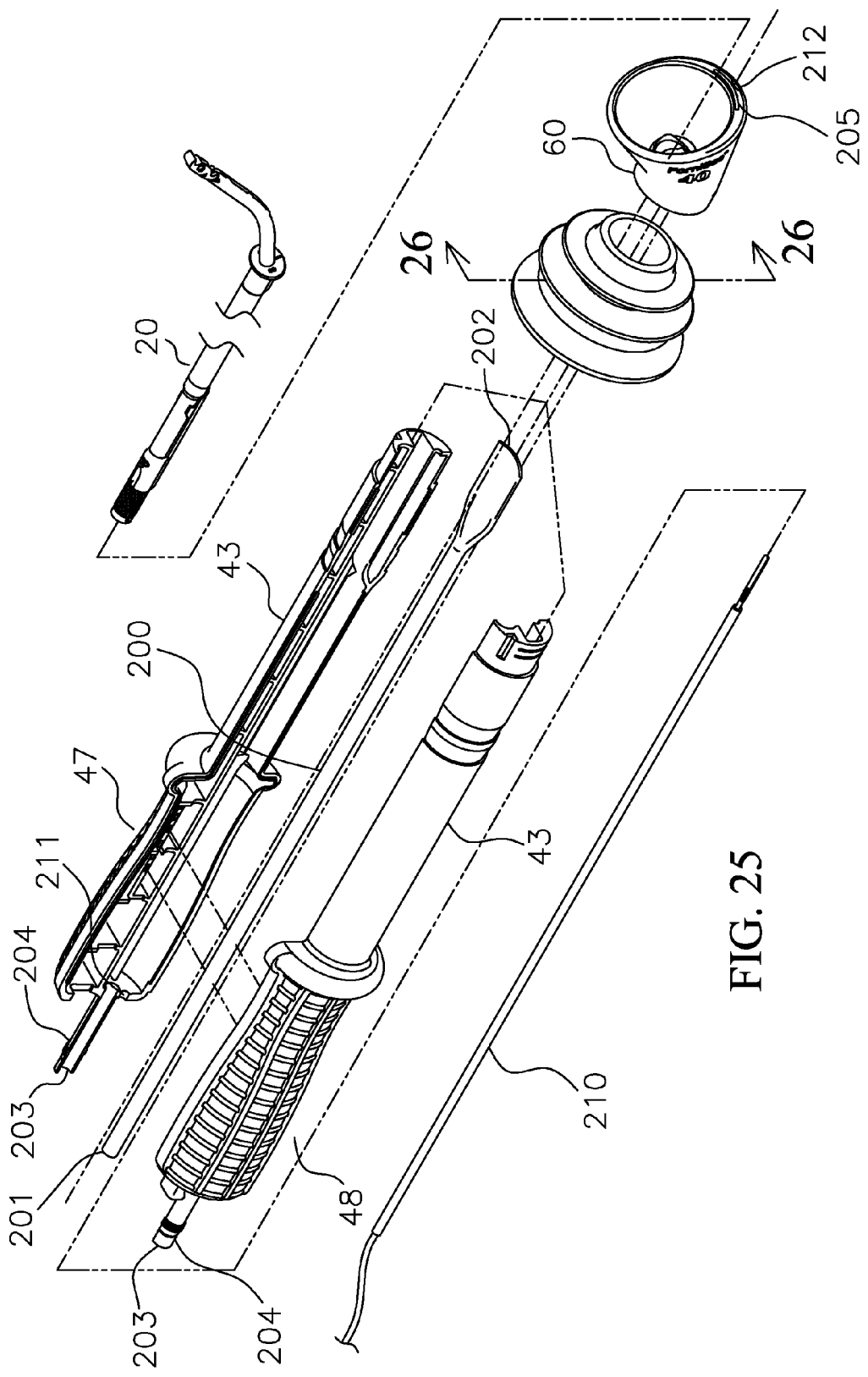
FIG. 25 is an exploded perspective view of an additional embodiment of the instrument wherein a light pipe and cautery wand are integrated within said invention.

FIG. 25 is an exploded perspective view of an embodiment incorporating an integrated light pipe 200, similar to the light wand 30, and cautery wand 210. The light pipe 200 is permanently captured between the assembled left handle 47 and right handle 48 such that the proximal face 201 is flush with the entry port 203 of the adapter halves 204, that when assembled serve as the connection point for most commercial light sources. The light pipe 200 proceeds through the shaft 43 and cup 60 until the distal face 202 is flush with and sealed tightly within a light port 205 of the cup 60. The light pipe 200 is typically molded from optically clear polymers such as medical grade polymethyl methacrylate (PMMA) acrylic whose end faces are highly polished to provide for maximum light transmissivity. In other embodiments, a powered light source may be provided to emit light proximate the cup 60. For example, a Light Emitting Diode could be provided in the cup 60 or a battery-operated light source could be provided, with batteries disposed in the device 40.

The cautery wand 210 is similar to the likes of commercially available wands such as the E1551G Blade Electrode from ValleyLab of Boulder, Colo., and is simply inserted through a wand port 211, traverses the shaft 43 and exits an electrode port 212 in the cup 60. Any known cautery may be used.

Figure 26:
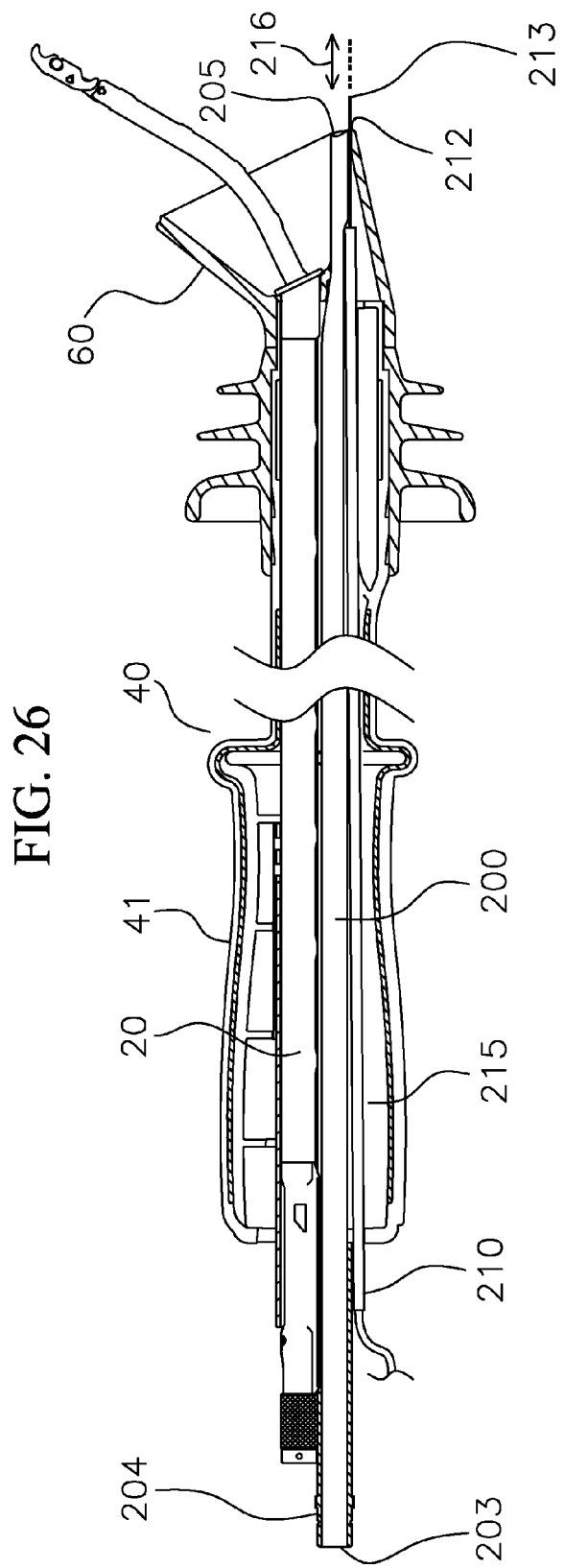
FIG. 26 is an orthogonal cross sectional view along lines 26-26 of the embodiment presented in FIG. 25 demonstrating the integration of the light pipe and cautery wand.

FIG. 26 is an assembled orthogonal section view taken along lines 26-26 of FIG. 25 illustrating the integration of the light pipe 200 within the textured handle 41 of the device 40 where the light pipe 200 is fixedly located coplanar and adjacent to the sound 20 such that the proximal face 201 is flush with the entry port 203 and, similarly, the distal face 202 is flush with the light port 205. Situated immediately below the light pipe 200 is the cautery wand 210 that is readily inserted through the wand port 211, traverses a wand channel 215, and exits the electrode port 212 through the cup 60. The cautery wand is movable in the wand channel 215, allowing linear motion in direction 216, thereby making a cautery tip 213 protuberate only at the surgeon's discretion or when surgical conditions dictate.

Figure 27:
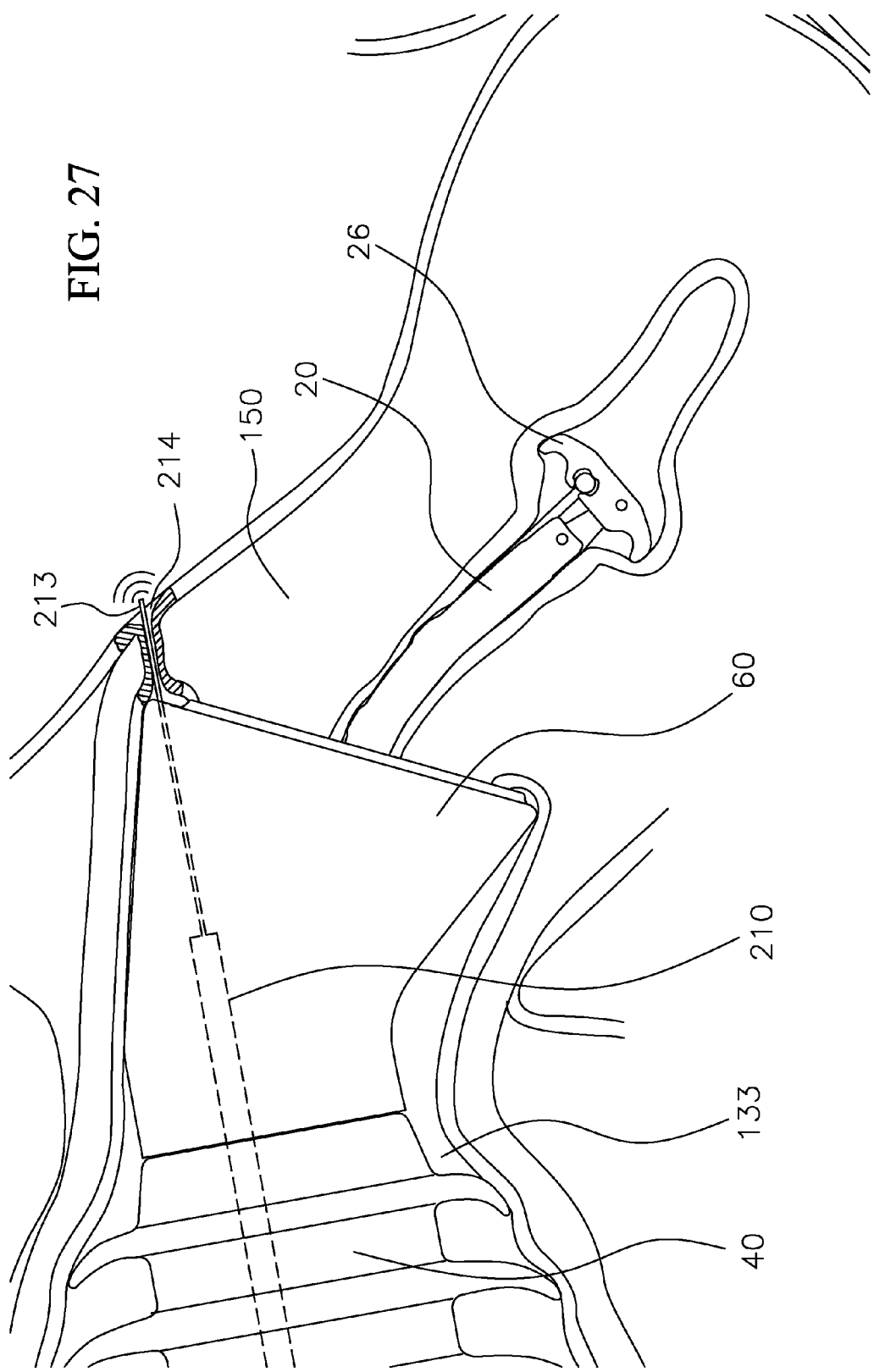
FIG. 27 is an anatomical sagittal view depicting an energized cautery wand of FIG. 25, presented in its preferred method of use, separating the uterus from the vagina as in a traditional colpotomy.

FIG. 27 is a sagittal view in which the cautery wand 210 is installed in the device 40 such that a wand tip 213 exits the cup 60. With the wand tip 213 energized, an incision 214 is made between the uterus 150 and vagina 133 while the rotational anchor 26 of sound 20 retains the uterus 150 in relation to the cup 60 of device 40.

Those of ordinary skill in the art will understand that modifications can be made to the foregoing embodiments. For example, although the sound, light wand and cautery wand are provided as items that are selectively inserted and removed from the device, any or all of them may be fixed as integral parts of the device. Moreover, the device may have additional passageways formed therethrough. For example, the device may include a cannula passageway adapted for receiving conventional surgical ports or other instruments.

The foregoing embodiments of the present invention are provided as exemplary embodiments and are presently best modes for carrying out the invention. Modifications of these embodiments will be readily apparent to those of ordinary skill in the art. The invention is not intended to be limited by the foregoing embodiments, but instead is intended to be limited only by the appended claims.

The invention claimed is:

1. A uterine manipulator comprising:
a sound having a selectively actuatable anchor disposed proximate a distal end, the anchor moveable between a deployed position and a delivery position, and an operating mechanism spaced from the anchor for selectively moving the anchor between the delivery position and the deployed position; and
a body comprising an outer surface having a plurality of ridges positioned on the outer surface and further having a passage therethrough adapted to receive the sound and the operating mechanism, the operating mechanism configured to pass proximally through the body to a position in which the operating mechanism is accessible proximally of the body and the anchor extends distally, the operating mechanism moving the anchor between the delivery position and the deployed position independent of the body;
further comprising a cup disposed at a distal end of the body and adapted to engage a uterus, wherein the distal end of the sound extends distally from the cup for insertion into the uterus;
further comprising a vaginal occluder surrounding the body proximal the cup, moveable along the body relative to the cup and configured to engage the ridges on the outer surface of the body in order to create an air tight seal.

2. The manipulator of claim 1, wherein the passage extends longitudinally through the body.

3. The manipulator of claim 1, wherein the body comprises a handle and a shaft arranged substantially coaxially.

4. The manipulator of claim 1, wherein a rim of the cup is angled relative to the body's longitudinal axis.

5. The manipulator of claim 4, further comprising an orientation indicator on the handle for indicating to a user an orientation of the cup.

6. The manipulator of claim 1, further comprising a light conduit disposed in the body for emitting light substantially distally.

7. The manipulator of claim 6, wherein the light conduit is selectively removable from the body through a port in the proximal end of the body.

8. The manipulator of claim 1, the body further comprising a cannula passage for receiving and passing a cannula.

9. The manipulator of claim 1, further comprising a cautery tip selectively protruding distally from the body.

10. A uterine manipulator comprising:
a generally straight, elongate body comprising an outer surface having a plurality of ridges positioned on the outer surface and further having a longitudinal axis and defining a substantially linear passageway therethrough;
a handle on one end of the body having a longitudinal axis substantially co-axial with the longitudinal axis of the body;
a cup on an opposite end of the body; and
a sound having an elongate shaft receivable in the substantially linear passageway of the elongated body and an angled shaft extending from the elongate shaft, a distal tip on the angled shaft protruding from the opening in the cup, and an operating mechanism coupled to a proximal end of the elongate shaft, the operating mechanism sized and configured to pass proximally through the body,
wherein the cup has an opening angled relative to the longitudinal axis of the elongate body;
further comprising a vaginal occluder surrounding the body proximal the cup, moveable along the body relative to the cup and configured to engage the ridges on the outer surface of the body in order to create an air tight seal.

11. The uterine manipulator of claim 10, wherein the sound further comprises an anchor on the distal end protruding from the body and the operating mechanism comprising an actuator to manipulate the anchor proximate the handle.

12. The manipulator of claim 10, wherein the elongate body is substantially coaxial with the handle from the proximal end to the cup.

13. The manipulator of claim 10, the cup being adapted to engage a uterus proximate the cervix and the occluder circumscribing and substantially sealing a vaginal opening when the cup is engaged with the uterus.

14. The manipulator of claim 10, wherein the sound is selectively removable from the distal end of the elongate body.

15. A surgical method of using the manipulator of claim 10, comprising:
inserting the sound into a uterus;
with the sound inserted in the uterus, passing the body distally over the sound so that the sound passes proximally through the passage in the elongate body to a position at which the cup contacts an outer wall of the uterus; and
rotating the body about its longitudinal axis to manipulate the uterus.

16. The method of claim 15, further comprising deploying an anchor provided on the sound with the sound inserted in the uterus.

17. A uterine manipulator comprising:
a shaft having a passageway therethrough, the shaft comprising a proximal handle and a distal angled cup, the shaft further comprising an outer surface extending between the handle and the cup, the outer surface having a plurality of ridges;
a vaginal occluder surrounding the shaft proximal the cup, moveable along the shaft relative to the cup and configured to engage the ridges on the outer surface of the shaft in order to create an air tight seal;
a sound comprising an elongate body having an elongate shaft portion and an angled shaft portion; an anchor disposed at a distal end of the angled shaft portion of the body and rotatable about a pivot point for selective placement between a first position generally aligned with the angled shaft portion of the body proximate the distal end of the angled shaft portion of the body and a second position substantially perpendicular to the angled shaft portion of the body proximate the distal end of the angled shaft portion of the body;
an operating mechanism carried by the body, the operating mechanism comprising a rotatable sleeve, concentric with the elongate shaft portion of the body and disposed along the body proximally of the anchor for receiving a user actuation;

and a mechanical link between the anchor and the operating mechanism adapted to selectively move the anchor between the first position and the second position upon user actuation;

the sound configured to pass proximally through the passageway.

18. The sound of claim 17, the anchor comprising fingers protruding therefrom.

19. The sound of claim 17, wherein the operating mechanism is rotatable to selectively move the anchor between the first position and the second position.

20. The sound of claim 17, wherein the elongate shaft portion and the angled shaft portion have a permanent fixed angulation.

* * * * *